(12) United States Patent
Muller

(10) Patent No.: US 10,603,192 B2
(45) Date of Patent: Mar. 31, 2020

(54) PROSTHETIC LINER AND PROSTHETIC SHAFT SYSTEM COMPRISING PROSTHETIC LINER AND PROSTHETIC SHAFT

(71) Applicant: OTTO BOCK HEALTHCARE GMBH, Duderstadt (DE)

(72) Inventor: Andre Muller, Duderstadt (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 0 days.

(21) Appl. No.: 14/895,254

(22) PCT Filed: May 30, 2014

(86) PCT No.: PCT/EP2014/001461
§ 371 (c)(1),
(2) Date: Dec. 2, 2015

(87) PCT Pub. No.: WO2014/194998
PCT Pub. Date: Dec. 11, 2014

(65) Prior Publication Data
US 2016/0120665 A1 May 5, 2016

(30) Foreign Application Priority Data
Jun. 3, 2013 (DE) .......... 10 2013 009 196

(51) Int. Cl.
*A61F 2/80* (2006.01)
*A61F 2/78* (2006.01)

(52) U.S. Cl.
CPC .............. *A61F 2/80* (2013.01); *A61F 2/7812* (2013.01); *A61F 2002/805* (2013.01); *A61F 2002/807* (2013.01); *A61F 2210/009* (2013.01); *A61F 2210/0057* (2013.01)

(58) Field of Classification Search
CPC .................................. A61F 2/80; A61F 2/7812
See application file for complete search history.

(56) References Cited

U.S. PATENT DOCUMENTS

| 2,464,443 | A | * | 3/1949 | Ganoe | A61F 2/68 623/26 |
| 4,655,779 | A | * | 4/1987 | Janowiak | A61F 2/80 623/37 |
| 5,464,443 | A | * | 11/1995 | Wilson | A61F 2/7843 623/36 |

(Continued)

FOREIGN PATENT DOCUMENTS

| CN | 1147370 A | 4/1997 |
| CN | 1838928 A | 9/2006 |

(Continued)

OTHER PUBLICATIONS

PCT International Search Report for PCT International Patent Application No. PCT/EP2014/001461, dated Jul. 17, 2014.

*Primary Examiner* — Bruce E Snow
*Assistant Examiner* — Melissa A Hoban
(74) *Attorney, Agent, or Firm* — Holland & Hart LLP

(57) ABSTRACT

A prosthetic liner for application on a stump, comprising an elastic base, which has a proximal opening for insertion of the stump in a receiving space, and a distal end. At least one pneumatic piston is arranged on the outer face of the prosthetic liner.

23 Claims, 19 Drawing Sheets

(56) References Cited

U.S. PATENT DOCUMENTS

| | | | |
|---|---|---|---|
| 5,728,170 A | 3/1998 | Becker | |
| 6,063,125 A | 5/2000 | Arbogast et al. | |
| 6,454,812 B1 | 9/2002 | Laghi | |
| 6,979,355 B1 | 12/2005 | Slemker | |
| 7,427,297 B2 | 9/2008 | Patterson | |
| 8,197,555 B2 | 6/2012 | Laghi | |
| 8,308,815 B2 | 11/2012 | McCarthy | |
| 9,119,735 B2* | 9/2015 | Accinni | A61B 5/4851 |
| 2002/0087215 A1* | 7/2002 | Caspers | A61F 2/5046 623/34 |
| 2002/0103544 A1* | 8/2002 | McDowell | A61F 2/78 623/33 |
| 2003/0195636 A1* | 10/2003 | Coop | A61F 2/78 623/36 |
| 2004/0002846 A1 | 1/2004 | Lutz et al. | |
| 2004/0028467 A1* | 2/2004 | Currier | A61F 2/7812 403/278 |
| 2004/0098136 A1* | 5/2004 | Caspers | A61F 2/5046 623/34 |
| 2007/0055383 A1* | 3/2007 | King | A61F 2/68 623/34 |
| 2008/0004716 A1 | 1/2008 | Hoerner | |
| 2009/0043402 A1 | 2/2009 | Slemker | |
| 2010/0026226 A1 | 2/2010 | Ritter et al. | |
| 2010/0070051 A1 | 3/2010 | Carstens | |
| 2011/0022183 A1* | 1/2011 | Slemker | A61F 2/78 623/34 |
| 2011/0035027 A1 | 2/2011 | McCarthy | |
| 2012/0191217 A1 | 7/2012 | Mackenzie | |
| 2015/0032226 A1* | 1/2015 | Hillmann | A61F 2/7812 623/32 |
| 2015/0202060 A1 | 7/2015 | Muller et al. | |
| 2016/0058583 A1* | 3/2016 | Hines | A61F 2/80 623/34 |

FOREIGN PATENT DOCUMENTS

| | | |
|---|---|---|
| CN | 101594837 A | 12/2009 |
| DE | 102004056775 A1 | 6/2006 |
| DE | 102006054891 A1 | 6/2008 |
| GB | 2486817 A | 6/2012 |
| RU | 2021787 C1 | 10/1994 |
| RU | 2325878 C1 | 6/2008 |
| WO | 2014032802 A1 | 3/2014 |

* cited by examiner

PROSTHETIC LINER AND PROSTHETIC SHAFT SYSTEM COMPRISING PROSTHETIC LINER AND PROSTHETIC SHAFT

TECHNICAL FIELD

The invention relates to a prosthetic liner for application on a stump, comprising an elastic base body which has a proximal opening, for insertion of the stump into a receiving space, and a distal end, and also a prosthetic socket system comprising such a prosthetic liner and prosthetic socket.

BACKGROUND

Prostheses are used to replace the function and optionally the visual appearance of a missing limb and are attached to the body of the patient. A variety of possibilities for attaching the prosthesis are known. A common possibility for attaching prostheses to extremities is the arrangement on a remaining part of the limb, the so-called stump. The stump is encompassed by a prosthetic socket, which in general is dimensionally stable. An insertion opening is formed on the proximal end of the socket, at least one fixing mechanism is provided on the distal end of the socket, on which further prosthetic components may be arranged, for example joints or other functional units such as prosthetic feet or prosthetic hands. In order to achieve a good fit, a model of the stump is prepared and the socket is adapted to the contour of the stump model. To compensate for variations in volume, it may be provided that the socket is made narrower than the molded stump model.

To increase comfort, it may be provided that a so-called prosthetic liner is arranged between the prosthetic socket and the stump. In general, the prosthetic liner comprises a closed base body with a proximal opening and is pulled over the stump in the manner of a sock. The elastic material adheres to the stump surface and generates the connection between the stump and the prosthetic socket. For attaching the prosthetic liner to the prosthetic socket, mechanical locking elements may be provided at the distal end of the prosthetic liner and corresponding locking mechanisms may be provided at the distal end of the prosthetic socket, which positively lock the prosthetic liner to the prosthetic socket after insertion into the prosthetic socket. The attachment of the prosthetic liner to the prosthetic socket can be released via an unlocking mechanism.

A further possibility for attaching a prosthetic socket to a stump resides in so-called suction socket liner technology, in which the prosthetic socket seals airtight against the prosthetic liner and the air present in the space between the prosthetic liner and the prosthetic socket is sucked or pressed out. Reverse flow is prevented by a non-return valve. It is necessary here to design the prosthetic socket in an airtight manner and to ensure a large sealing area against the prosthetic liner.

US 2011/0035027 A1 relates to a vacuum-assisted liner system with a flexible liner, which is pulled over a stump and which has at least one peripheral edge. The liner is made of an airtight material and has at least one porous region which is spaced apart from the peripheral edge, in order to enable the transport of air and moisture between an outer surface and an inner surface of the liner.

US 2012/0191217 A1 relates to a socket system with a vacuum liner for prosthetic or orthotic devices. A region of elastic material is arranged on the distal end of the closed liner, which material is harder than the material of the rest of the liner. The region has a concave section which extends inward from an outer end surface of the region. The distal region and the concave section form at least a part of a vacuum pump, in order to pump air out of the space between the liner and the prosthetic socket.

U.S. Pat. No. 8,197,555 B1 relates to a vacuum pump which is integrated into a prosthetic socket on the distal end thereof. The vacuum pump comprises an elastomer housing with two non-return valves and a spring element made from an elastomeric material. If the spring element is loaded, air is forced through a first non-return valve into an intermediary space and out of an outlet valve from the intermediary space into the environment. If the elastomeric spring element is unloaded, the outlet valve is closed and the first non-return valve is opened, and further air is sucked out of the prosthetic socket into the intermediary space. The air in the intermediary space between the prosthetic socket and the prosthetic liner is thereby pumped out.

U.S. Pat. No. 6,979,355 B1 relates to a valve arrangement for a prosthetic mechanism with a prosthetic socket, on the distal end of which is formed a channel which is closed with a valve.

U.S. Pat. No. 6,063,125 relates to an attachment mechanism for prosthetic limbs with a socket and a distal adapter, in which a through-bore is arranged. A non-return valve is formed within the bore.

DE 10 2006 054 891 A1 relates to a prosthetic socket with active air discharge, in which a pump chamber is arranged in a side wall of a prosthetic socket and is coupled via a valve to the external environment.

US 2008/0004716 A1 relates to a socket and a liner for attachment to a stump. A non-return valve is formed in the socket to transport air out of the socket.

DE 10 2004 056 775 A1 relates to a device for releasably connecting a prosthetic socket to a prosthetic lower part. A spring-loaded piston is guided in a piston chamber at the distal end of the prosthetic socket. A seal may be arranged on the piston to create a negative pressure in conjunction with a valve in the piston chamber. Elastically pretensioned latching means are assigned to the piston in order to limit the movement thereof, said latching means latching into latching recesses formed in the piston.

SUMMARY

The object of the present invention is to provide a prosthetic liner and a prosthetic socket system, with which a secure attachment of the prosthesis to the liner can be achieved for passive vacuum sockets, and which can provide an improved feeling of retention and also an improved wearing comfort for the user.

According to the invention, this object is achieved by a prosthetic liner with the features of the main claim and a prosthetic socket system with the features of the additional independent claim. Advantageous refinements and developments of the invention are disclosed in the dependent claims, the figures and the description.

In the prosthetic liner for application on a stump, comprising an elastic base body which has a proximal opening, for insertion of the stump into a receiving space, and a distal end, provision is made that a pneumatic piston is arranged on the outside of the prosthetic liner.

In a passive vacuum system, i.e. a system in which a vacuum between a prosthetic liner and a prosthetic socket is created by the wearer of the prosthetic himself and the relative movement of the prosthetic liner relative to the prosthetic socket, a negative pressure is created in the interior of the socket in the swing phase, in which the prosthetic mechanism is moved away from the stump due to centrifugal forces. A retaining force is generated by means of the negative pressure in the interior of the socket during the swing phase, which retaining force is responsible for the attaching effect of the prosthetic liner in the prosthetic socket. This movement can be perceived by users as uncomfortable, because the lifting of the prosthetic socket and the liner leads to a feeling of instability and loose fit. The air from the space between the prosthetic liner and prosthetic socket is evacuated by the pneumatic piston, which leads to an improved retaining force. The result is a self-regulating system, which is designed to ensure optimum retention between the prosthetic socket and the prosthetic liner. The pneumatic piston enables a precise guiding of the distal end of the liner with effective pumping action due to the simplified sealability of the volume closed off by the pneumatic piston.

A development of the invention provides that the pneumatic piston has a blocking element which prevents a reverse flow of air in the direction of the prosthetic liner. By the arrangement of a blocking element, for example a valve or circumferential blocking lip, in or on a pneumatic piston arranged at the distal end of the prosthetic liner, it is possible to use the relative movement between the prosthetic liner and the prosthetic socket to increase the negative pressure within the prosthetic socket and thereby to reduce the lifting of the prosthetic liner from the inner wall of the prosthetic socket. The air from the space between the prosthetic liner and prosthetic socket is evacuated by means of the piston, which leads to a compact structure in which essential components for the evacuation are integrated into the pneumatic piston.

The pneumatic piston may be configured as a separate component and attached to the prosthetic liner; in particular the respective pneumatic piston may be reversibly attached to the distal end or in the distal end region of the prosthetic liner. Through a reversible attachment or attachment possibility to the prosthetic liner, it is possible to attach different sized pneumatic pistons to the liner in order to enable an adaptation to the respectively necessary retaining force or the necessary pump volume. At least one attachment mechanism is formed on the prosthetic liner and correspondingly on the pneumatic piston for the reversible attachment of the pneumatic piston to the prosthetic liner. The attachment mechanism may be formed, for example, as a screw system, a click system with a ball head bearing, a positive locking via velcro closures or a hook system with corresponding receptacle and positive locking.

In addition to the reversible attachment of the pneumatic piston to the liner, it is possible to form this in one piece with the liner or to firmly bond it thereon. For this purpose, the pneumatic piston may be attached to the prosthetic liner via an elastic shaft, so that small misalignments between the pneumatic piston and the prosthetic socket-side receptacle can be compensated. By means of a one-piece configuration, it is possible to dispense with a separate mounting and a separate coupling element. In an elastic binding of the pneumatic piston to the prosthetic liner, a bringing together of the prosthetic liner with the prosthetic socket is facilitated, as slight misalignments of the pneumatic piston can be compensated by the material elasticity.

The blocking element assigned to the pneumatic piston is formed as a valve in or on the pneumatic piston or as a blocking lip functions similarly to an air pump and allows air to flow into the closed volume during a suction movement and comes into contact with the cylinder region during a discharge movement and thereby effects a seal.

In order to ensure a secure attachment of the pneumatic piston to the prosthetic liner and moreover to enable a sufficient stability and force distribution from the distal end of the prosthetic liner to the stump, a dimensionally stable end cap is provided on the distal end in a development of the invention, onto which the pneumatic piston is attached. The attachment may be carried out via the above-described attachment mechanisms. In principle, it is also possible that the pneumatic piston is formed on the distal end of the prosthetic liner or the end cap, so that a very compact construction results.

The pneumatic piston may have at least one circumferential sealing element, in particular an O-ring, by means of which the volume between the pneumatic piston and the cylinder region of the prosthetic socket can be sealed. In principle, it is also possible and provided that the piston may also function without a sealing element in the cylinder region, if the accuracy of fit is sufficiently high.

A development of the invention provides that the pneumatic piston is movably attached to the prosthetic liner, for example via a ball joint or an elastomeric element. The movable attachment may here occur directly on the prosthetic liner or on an end cap arranged thereon. By means of a ball joint, it is possible that the pneumatic piston may always be moved perpendicularly within a corresponding cylinder region in the prosthetic socket, without a tilting of the pneumatic piston within the cylinder region. At the same time, a reversible connection between the pneumatic piston and the prosthetic liner may occur via the ball joint, since the prosthetic liner-side attachment element is formed as a ball head, onto which a pneumatic piston, which has been provided with a corresponding receptacle, is clipped. In addition to a mounting via a ball joint, which in general enables a rotation about a pivot without resetting forces, an elastic connection of the pneumatic piston to the prosthetic liner is possible, for example via an elastic web, pins, bolts or the like. In addition to a relative displaceability of the pneumatic piston to the prosthetic liner, a guiding and centering within the prosthetic socket is also provided by the elastic connection.

A development of the invention provides that the pneumatic piston is attached to the prosthetic liner via at least one magnet. Via the magnetic, i.e. force-locking, attachment of the pneumatic piston to the prosthetic liner, for example to a pin of an end cap, it is possible to easily connect different prosthetic liners to the pneumatic piston, so that a standardized pneumatic unit can be coupled to different prosthetic liners, or vice versa. By means of the magnetic coupling, it is also possible to perform a relatively easy replacement of individual components.

In one embodiment of the invention, the pneumatic piston is or can be connectably integrated via at least one magnet into a prosthetic socket system composed of the prosthetic liner, in particular as it is described above, and a prosthetic socket.

In order to allow a displaceability similar to that of a ball joint in a magnetic connection of the pneumatic piston to the prosthetic liner, such that the pneumatic piston itself can always be guided straight into the receiving part, in particular in the cylindrical region of the receiving part, a spherical surface is provided at least in parts on the pneumatic piston, which surface may either be convex or concave. A movability and a certain displaceability is possible by means of the spherical surface due to the magnetic connection, so that rotational forces are not directly transferred to the pneumatic piston, so that a canting cannot take place, or only takes place in extreme situations.

An attachment element may be arranged on the prosthetic liner, via which element the pneumatic piston is attached to the prosthetic liner and which has a contact surface formed to correspond to an at least partially spherical surface of the pneumatic piston. Through the convex contact surface in a concavely-formed spherical surface of the pneumatic piston or vice versa, it is possible to perform a ball joint-like movement of the pneumatic piston about the attachment element, so that a relative displacement of the prosthetic liner to the pneumatic piston with respect to the possible axes of rotation is always provided.

The connection between the prosthetic liner and the pneumatic piston may occur as the user gets into the prosthetic socket, so that as soon as the user of the prosthesis gets into the prosthetic socket, the prosthetic liner or the attachment element brings the contact surface into contact with the magnets on or in the pneumatic piston. Even when the piston is at rest in the lower position, the magnetic forces are generally sufficient to move the piston back to the upper position. In general, however, the pneumatic piston is in the upper position, because the piston is located there when the prosthetic socket is exited. When the prosthesis user exits the prosthetic socket, a separation of the prosthetic liner from the pneumatic piston may easily occur through a pulling-out movement, which merely has to apply a force which is greater than that exerted by the retaining magnets in the pneumatic piston or in the attachment element.

In the prosthetic socket system having a prosthetic liner for application on a stump, comprising an elastic base body which has a proximal opening, for insertion of the stump into a receiving space, and a distal end, and a prosthetic socket which forms an intermediary space with the prosthetic liner, provision is made that at least one pneumatic piston is arranged on the outside of the prosthetic liner and that the prosthetic socket has a cylinder region corresponding to the pneumatic piston, which cylinder region is formed to receive the pneumatic piston and in which a closed volume is formed in the coupled state of the prosthetic liner with the prosthetic socket, which closed volume is coupled to at least one blocking element which prevents a reverse flow of air into the intermediary space. The prosthetic liner may be designed as described above or may also function without an integrated valve or integrated blocking lip in a corresponding design of the cylinder region. The corresponding cylinder region is formed such that the pneumatic piston may glide on the inside of the prosthetic liner along a sealing element, in order to push air out of the closed volume.

According to the invention, it is provided that the pneumatic piston forms a closed volume together with the corresponding cylinder region on the prosthetic socket, which closed volume, by means of a blocking element, in particular a non-return valve, draws air in from the region between the prosthetic socket and the prosthetic liner during a volume expansion, for example during the swing phase, and expels it again by means of an equally oriented non-return valve, for example on the end of the cylinder region opposite the pneumatic piston, during the stance phase, when an axial loading in the direction of the distal end of the prosthetic socket occurs. The closed volume, which is variable due to the relative displacement between the cylinder region and the pneumatic piston, represents the pumping volume which corresponds to the maximum expulsion volume of a full stroke. The larger the diameter of the pneumatic piston and the greater the possible stroke, the greater the pumping volume and thereby the negative pressure between the prosthetic socket and the prosthesis liner achievable per stroke.

Within the volume, at least one blocking mechanism or at least one fluidic connection to a blocking mechanism may be present, which enables an outflow of air and prevents a reverse flow. This is possible, for example, by means of a non-return valve, which can optionally also be opened in order to reduce the negative pressure and the retaining force. By means of the arrangement of a blocking mechanism, an almost silent evacuation is possible, in addition to which it is possible to define the location at which the air is pressed out of the volume. The blocking mechanism or blocking mechanisms enable a suction of the air out of the intermediary space between the prosthetic liner and the prosthetic socket, and they prevent a reverse flow of air from the environment through the closed volume into the intermediary space.

The closed volume and/or the intermediary space may be fluidically connected to a ventilation mechanism for the introduction of air, in order to cancel the negative pressure in the closed volume or intermediary space and to introduce ambient air into the closed volume and/or intermediary space between the prosthetic socket and the prosthetic liner, so that the prosthetic liner can be removed from the prosthetic socket. The ventilation mechanism has an access to the closed volume and/or directly to the intermediary space of prosthetic liner and prosthetic socket, in order to enable a release of the connection. Alternatively to the use of a ventilation mechanism, the intermediary space may be ventilated by removal of a sealing collar, which is used as a proximal seal. If a seal is arranged in the socket or arranged on the liner, a separate ventilation mechanism is necessary.

An insertion bevel may be provided on the proximal end of the cylinder region to facilitate insertion of the pneumatic piston into the cylinder region, so that the correct relationship between the stump with prosthetic liner and the prosthetic socket can be easily created. The pneumatic piston is automatically guided to the cylinder region via the insertion bevel, and the latter ensures a centering and orienting of the prosthetic liner within the prosthetic socket.

A pull-out safety for the pneumatic piston may be arranged on the proximal end of the cylinder region, preventing the pneumatic piston from being pulled out of the cylinder region during a withdrawal from the prosthetic socket. The pull-out safety may be arranged mechanically, in particularly form-lockingly, on the receiving part, for example screwed, clamped or clipped in. Advantageously, a circumferential configuration of the pull-out safety is provided by means of a screwed-on or otherwise fixed ring.

BRIEF DESCRIPTION OF THE DRAWINGS

Exemplary embodiments of the invention are explained hereinafter in detail with reference to the accompanying figures. Like reference signs refer to like components.

DETAILED DESCRIPTION

Figure 1:
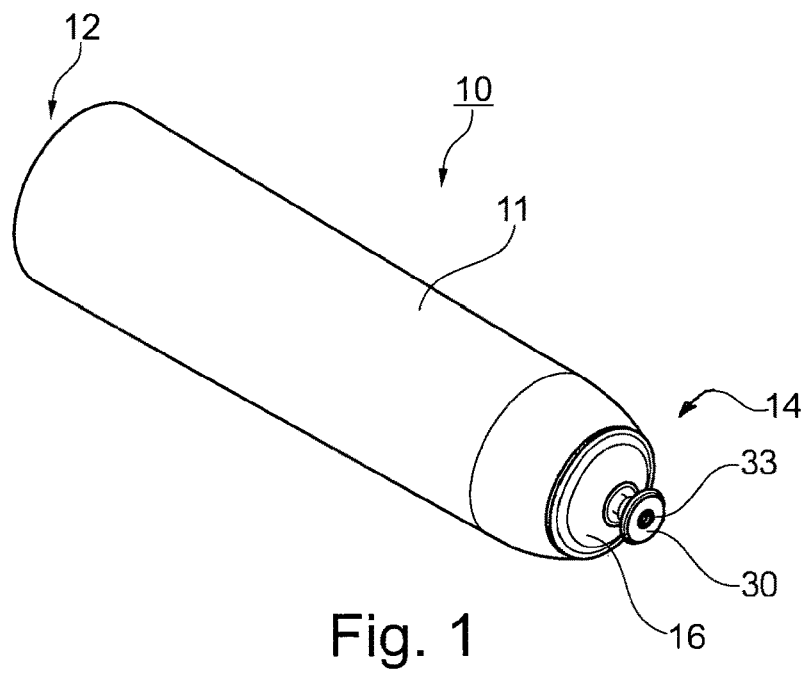
FIG. 1 shows a schematic representation of a prosthetic liner and a pneumatic piston in a side view.

FIG. 1 shows a prosthetic liner 10 with an elastic base body 11, which may be made for example of silicone or another elastomer. An opening is present at the proximal end 12 of the prosthetic liner, through which opening a prosthesis user may place a stump in a receiving space within the prosthetic liner 10. The receiving space is not shown in this figure. In general, the application of the prosthetic liner 10 takes place by means of a rolling down of the proximal end 12 or by eversion of the proximal end 12, application of a distal end 14 of the prosthetic liner to the distal end of the stump and then rolling onto the stump. In the example shown, a dimensionally stable end cap 16 is arranged on the distal end 14 of the prosthetic liner 10, which end cap 16 is used to stabilize and soften the bedding of the stump with respect to the connection of a pneumatic piston 30 on the outside 15, i.e. the side of the prosthetic liner 10 opposite the receiving space. Attachment mechanisms arranged on the end cap 16 make it possible to arrange the pneumatic piston 30 on the end cap 16. The pneumatic piston 30 likewise has an attachment mechanism 37, via which the pneumatic piston 30 can be attached to the prosthetic liner 10, in particular to the distal end cap 16.

Figure 2:
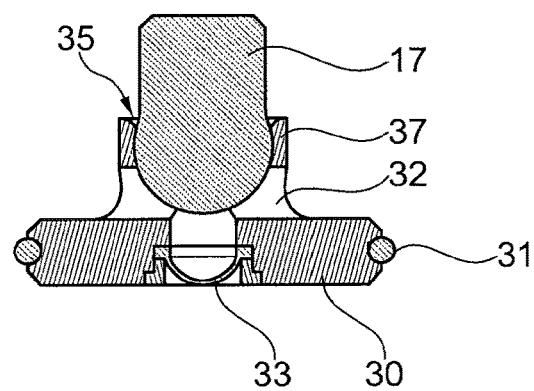
FIG. 2 shows a sectional view of a pneumatic piston.

The underside of the pneumatic piston 30 can be seen in FIG. 2; the sealing element 31 at the outer periphery of the pneumatic piston 30 can likewise be seen. Through the arrangement of the sealing element 31 on the outer periphery of the pneumatic piston 30, a sealing fitting on a cylinder region is possible, so that a pumping effect is brought about during a relative movement between the pneumatic piston 30 and the cylinder region. The pneumatic piston 30 can be reversibly connected via the attachment elements 17, 37 to the prosthetic liner 10. It is thereby possible to attach different types of pneumatic pistons to the liner. The pneumatic pistons 30 may vary in diameter, shape or choice of material. In place of a pin, the pneumatic piston 30 may also be screwed in, as a result of which it is possible to use a standard liner after corresponding conversion.

The coupling of the pneumatic piston 30 to the prosthetic liner 10 is preferably formed as a mechanical coupling, for example as a ball head joint 35; it is also possible that an adhesive connection is formed between the components. Alternatively to a separate embodiment of the pneumatic piston 30, it is possible to integrate this directly into the distal end cap 16, for example through integral forming or molding within the context of a two-component injection molding process. The end cap 16, which is also deformable to a certain extent, may be made from the material of the prosthetic liner 10 and may form a continuous system between the prosthetic liner 10 and the pneumatic piston 30 in a material connection to the pneumatic piston 30. It is also possible and provided that the attachment element 17 assigned to the prosthetic liner 10 is integrally formed with the prosthetic liner 10 or materially connected therewith, for example attached or formed onto the end cap 16.

It can further be seen in FIG. 2 that a fluidic connection 32 in the form of a transverse bore within the pneumatic piston 30 is formed on a projection or protrusion oriented toward the prosthetic liner 10. The transverse bore 32 opens into a bore which is oriented perpendicular to the main surface of the pneumatic piston 30, so that a fluidic connection 32 from the ambient atmosphere around the prosthetic liner 10 to the distal end face of the pneumatic piston 30 is present. A valve 33 in the form of a non-return valve is arranged within this fluidic connection 32 and permits a flow in the direction toward the distal end face of the pneumatic piston 30 but blocks a reverse flow through the fluidic connection 32. It is thereby possible that air from the environment around the prosthetic liner 10, for example from the space 60 between the prosthetic liner 10 and a prosthetic socket 20, can be suctioned out and transported into the environment, whereas penetration of air into this space 60 through the fluidic connection 32 is not possible. A plurality of transverse bores may be present, so that the fastening elements 37 may be formed as finger-like spring elements, in order to form the ball joint bearing 35.

In addition to only one sealing element 31 at the outer periphery, a plurality of sealing elements 31 which are spaced axially apart from one another may also be arranged at the outer periphery of the pneumatic piston 30, in order to permit improved guiding in a corresponding cylinder region 21 of a prosthetic socket 20.

Figure 3:
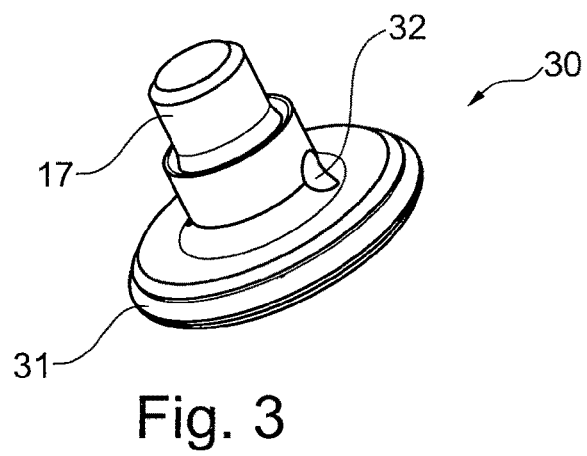
FIG. 3 shows a perspective view of a pneumatic piston.

FIG. 3 shows a perspective view of FIG. 2, which shows the separate embodiment of the pneumatic piston 30 on the attachment element 17. The attachment element 17 may be reversibly attached to the prosthetic liner 10, in particular the end cap 16.

Figure 4:
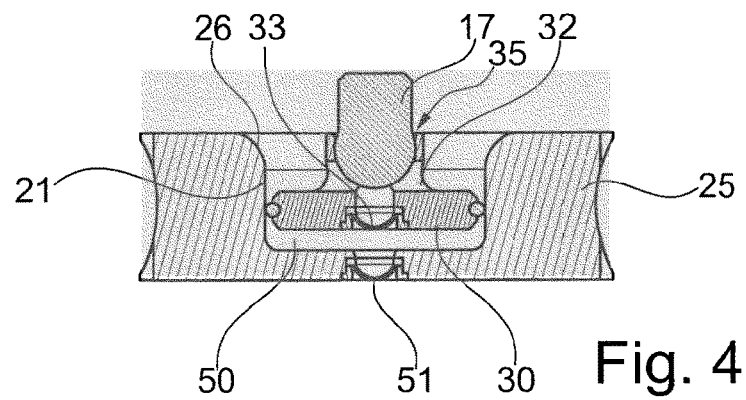
FIG. 4 shows a sectional view through a prosthetic liner during joining.

A sectional view of a detail representation is shown in FIG. 4, in which the pneumatic piston 30 according to FIG. 2 is inserted in a cylinder region 21 of a receiving part 25. The receiving part 25 and the cylinder region 21, which is formed therein, form the corresponding counterpart to the pneumatic piston 30, which sealingly bears with the sealing element 31 on the wall of the cylinder region 21. The pneumatic piston 30 closes the cylinder region 21 in the proximal direction and forms a closed volume 50 therewith, which has an outlet valve 51 in the form of a non-return valve, so that, during a relative movement between the receiving element 25 and the pneumatic piston 30 in the direction of the outlet valve 51, the air compressed in the closed volume 50 can be pressed out. If, in the case of an unloading, a relative movement of the pneumatic piston away from the outlet valve 51 takes place, air from the surrounding area of the prosthetic liner 10, not shown, is transported through the valve 33 into the closed volume 50 by means of the fluidic connection 32, since a positive pressure has formed relative to the closed volume 50. Via a reverse movement, the air which is located and compressed in the closed volume 50 is again discharged via the discharge valve 51.

An insertion bevel 26 is incorporated into the receiving part 25 on the proximal edge of the cylinder region 21, which insertion bevel 26 forms a radius in the embodiment shown, so that, even with a positioning of the prosthetic liner 10 in a prosthetic socket that is initially inaccurate, for example during insertion, a suitable and desired association between the pneumatic piston 30 and the cylinder region 21 can be realized.

Through the combination shown in FIG. 4 of a sealed pneumatic piston 30 and cylinder region 21, a piston pump is formed via which the air can be suctioned out of the surrounding area of the prosthetic liner 10, in particular out of the space between a prosthetic socket 20 formed as a suction socket and the prosthetic liner 10. If the suction and pumping process is repeated several times, the negative pressure within the prosthetic socket 20 changes with each piston stroke. Due to the reduction of play between the prosthetic liner 10 and the prosthetic socket 20, the piston stroke is gradually reduced, as a return movement of the pneumatic piston 30, i.e. an increase of the volume 50, is gradually reduced. Due to the direct mechanical coupling of the pneumatic piston 30 and the prosthetic liner 10, a stroke movement takes place until the prosthetic liner 10 no longer moves in the prosthetic socket 20. If this state is reached, it can be assumed that an optimum retaining force between the prosthetic liner 10 and the prosthetic socket 20 has been regulated, as the prosthetic liner 10 now lies flush against the inside of the prosthetic socket 20.

Figure 5:
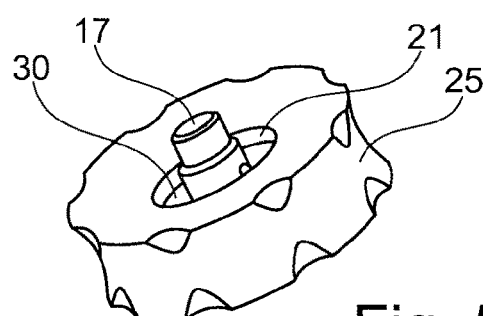
FIG. 5 shows a perspective view of a receiving part.

A three-dimensional perspective view of the receiving part 25 with the inserted pneumatic piston 30 and the attachment element 17, which is associated with the prosthetic liner 10, is shown in FIG. 5. The receiving part 25 may be attached to the prosthetic socket 20, not shown, and consist of a highly dimensionally stable material, for example a light metal or fiber-reinforced plastic, which is outfitted with a smooth surface in the cylinder region 21 or which has an insert, with which an appropriate friction pairing between the pneumatic piston 30 and the cylinder region 21 can be made. Mechanical attachment elements or receiving mechanisms for such attachment elements, for example threads, bores, undercuts or the like, may be arranged or formed on the receiving part 25. In principle it is also possible to attach the receiving part 25 to the prosthetic socket 20 by gluing, welding or velcro connections.

Figure 6:
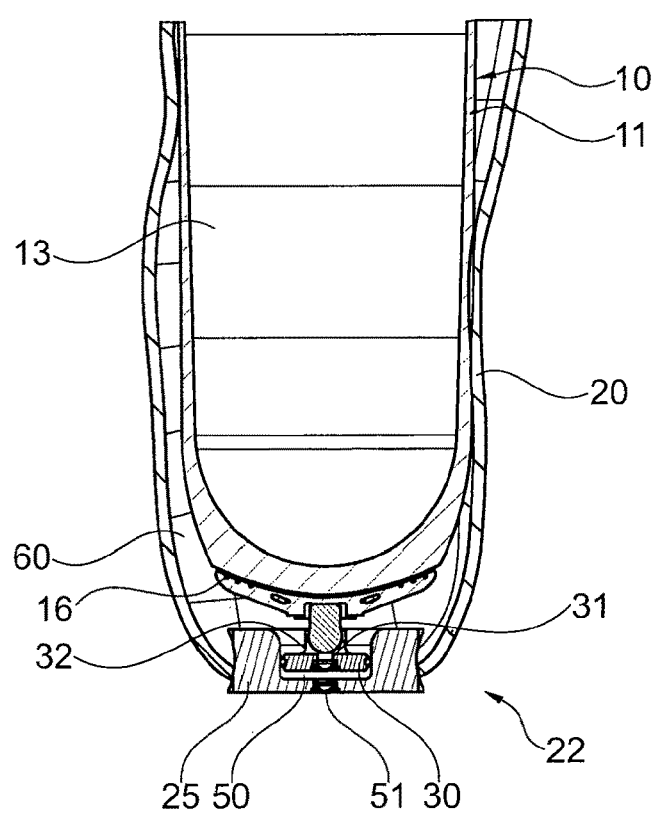
FIG. 6 shows a sectional view in the assembled state.

FIG. 6 shows in a sectional representation a prosthetic liner 10 with the distal end cap 16 and the pneumatic piston 30 inserted in the prosthetic socket and the use of the prosthetic liner 10 with the movably mounted pneumatic piston 30 arranged on the outside 15 thereof and attached thereon, in connection with a prosthetic socket 20. The prosthetic socket 20 is substantially formed according to the outer contour of the stump, not shown, and formed in the embodiment shown from a dimensionally stable, air-tight material, for example a fiber-reinforced plastic. The user puts on said prosthetic socket 20 with the prosthetic liner 10 and the pneumatic piston 30, which is reversibly attached at the distal end 14 or integrally formed, through the proximal opening of the prosthetic socket 20. A force is thereby applied to the pneumatic piston 30 through the application of the body weight in the distal direction. Even if the prosthetic socket 20 has an open space at its distal end, which makes a precise introduction of the pneumatic piston 30 in the cylinder region 21 more difficult, the pneumatic piston 30 may be securely inserted into the cylinder region 21 due to the insertion bevel 21. The attachment element 17 may be elastically formed, for example from a TPE, such that in this case a deformation of the attachment element 17 takes place during insertion of the pneumatic piston 30.

By means of body weight, the pneumatic piston 30 is inserted into the cylinder region 21 and the air within the closed volume formed thereby is expelled through the outlet valve 51. The outlet valve 51 is formed as a non-return valve or one-way check valve, which allows air or another medium out of the volume 50 but blocks admission into the volume 50 during a reverse movement of the pneumatic piston 30.

A volume is thereby spanned in the intermediary space 60 between the outside of the prosthetic liner and the inside of the prosthetic socket, which volume can be evacuated via the pneumatic piston 30 by a repeated application of force in the distal direction and a reverse unloading movement. Due to the resulting negative pressure, for example in a swing phase, a retaining force, albeit a small one, is also generated between the pneumatic piston 30 and the prosthetic socket 20, so that the prosthetic liner 10, which lies adhering to the skin of the stump, is held and guided on the prosthetic socket 20 by means of the pneumatic piston 30, to which the prosthetic liner 10 is mechanically coupled. The main retaining force is provided by the negative pressure in the space 60 between the prosthetic liner and the prosthetic socket.

The receiving space 13 for the stump of the prosthesis user is also shown in the sectional view of FIG. 6. Through the pressing movement in the distal direction, the pneumatic piston 30 is moved together with the prosthetic liner 10 in the direction of the distal end 22 of the prosthetic socket 20. The closed volume 50 present between the pneumatic piston 30 and the cylinder region 21 is compressed, the gas contained within the volume 50, generally air, is pressed out, and the prosthetic liner 10 can be pushed further in the direction of the distal end 22 of the prosthetic socket 20, until the pneumatic piston 30 has reached the base of the cylinder region 21 at the distal end 22.

If the end position of the prosthetic liner 10 and therefore also of the pneumatic piston 30 within the prosthetic socket 20 is reached and the volume 50 is minimized, a loading of the prosthetic liner 10 in the proximal direction leads to an increase in volume both of the closed volume 50 and also of the intermediary space 60, whereby a relative negative pressure results both with respect to the external environment and also to the intermediary volume between the prosthetic socket 20 and the prosthetic liner 10. This negative pressure on the one hand holds the pneumatic piston 30 in the cylinder region 21 and on the other hand suctions air from the intermediary space 60, which air, during loading, for example when taking a step, is pressed back out of the closed volume 50. A mechanical barrier, for example an adjustable stop, a locking pin or another type of motion limitation may be provided against unintentional sliding of the pneumatic piston 30 out of the cylinder region 21.

Figure 7:
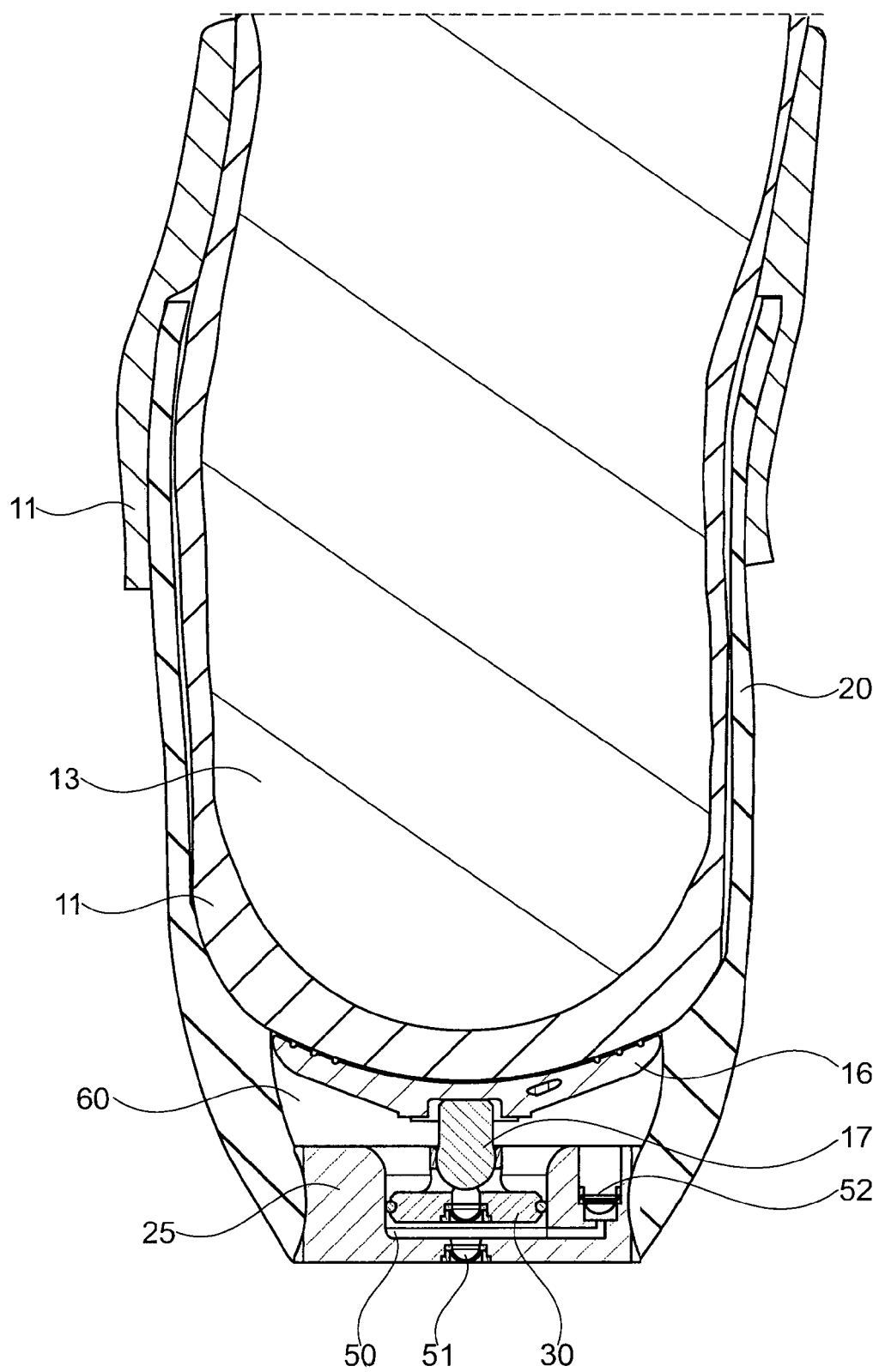
FIG. 7 shows a schematic view of one variant.

In FIG. 7, a variant of the invention is shown which substantially corresponds to the construction of the device according to FIG. 6. The prosthetic liner 10 is turned back on the outside around the proximal edge of the prosthetic socket 20 or provided with an outer sleeve which is fixed to the outside of the prosthetic liner 10 and which forms a gap, into which the prosthetic socket 20 can be inserted, so that sealing also takes place on the outside of the prosthetic socket 20. The turned-back prosthetic liner 10 or the sleeve arranged thereon are air-tightly formed; the sleeve may be glued, welded or pressed and adhered to the prosthetic liner 10. The volume enclosed by the prosthetic liner 20 and the prosthetic socket 10 is thereby maintained securely in the intermediary space 60.

Instead of a valve or blocking mechanism in the pneumatic piston 30, it is provided that the blocking element 52 is not arranged in the pneumatic piston 30, but rather within the receiving part 25, in which a fluidic connection from the intermediary space 60 to the closed volume 50 is present in the form of a channel. The channel connects the suction side of the pneumatic piston 30 to its pressure side. The blocking element 52 is arranged within this fluidic connection in the form of a non-return valve, which prevents a reverse flow of air from the pressure side to the suction side. In a pulling-out movement of the prosthetic liner 11 and thus a movement of the pneumatic piston 30 from the distal end position in the direction of the proximal insertion position, a negative pressure is created in the closed volume 50, through which air is suctioned from the intermediary space 60 into the closed volume 50. In an immersion movement of the pneumatic piston 30, the air in the closed volume is then fed out through the outlet valve 51.

Figure 8:
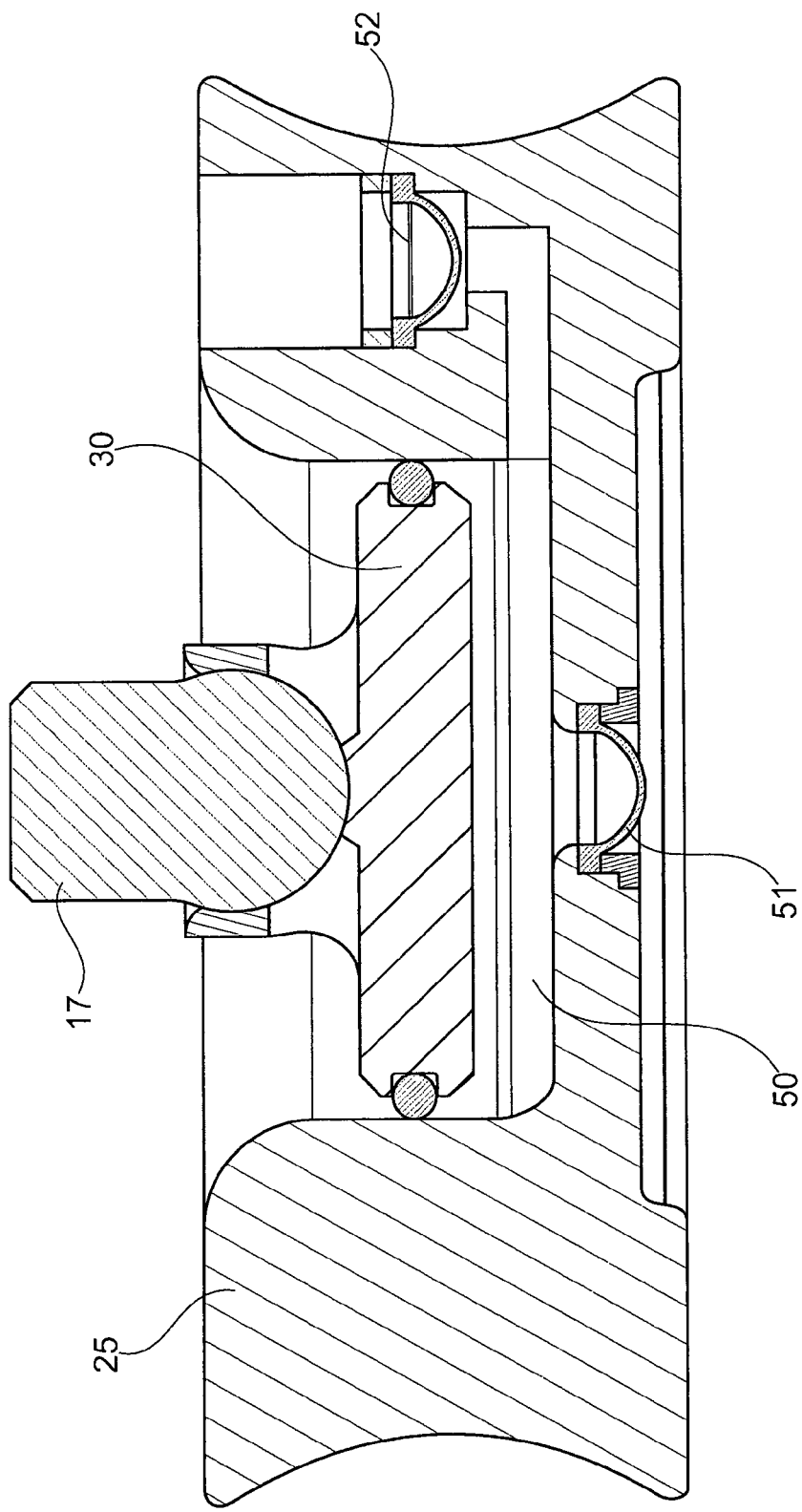
FIG. 8 shows a detail view of FIG. 7.

In FIG. 8, the receiving part 25 is shown in isolation with the pneumatic piston 30; the connecting channel between the intermediary space and the closed volume 50 is blocked via the blocking mechanism 52 against an outflow from the closed volume, so that a pumping out of air from the intermediary space 60 between the prosthetic socket and the prosthetic liner is possible. The arrangement of a non-return valve 52 in a separate channel at the receiving part 25 is advantageous with small dimensions of the pneumatic piston 30, as only a small installation space is available in the pneumatic piston.

Figure 9:
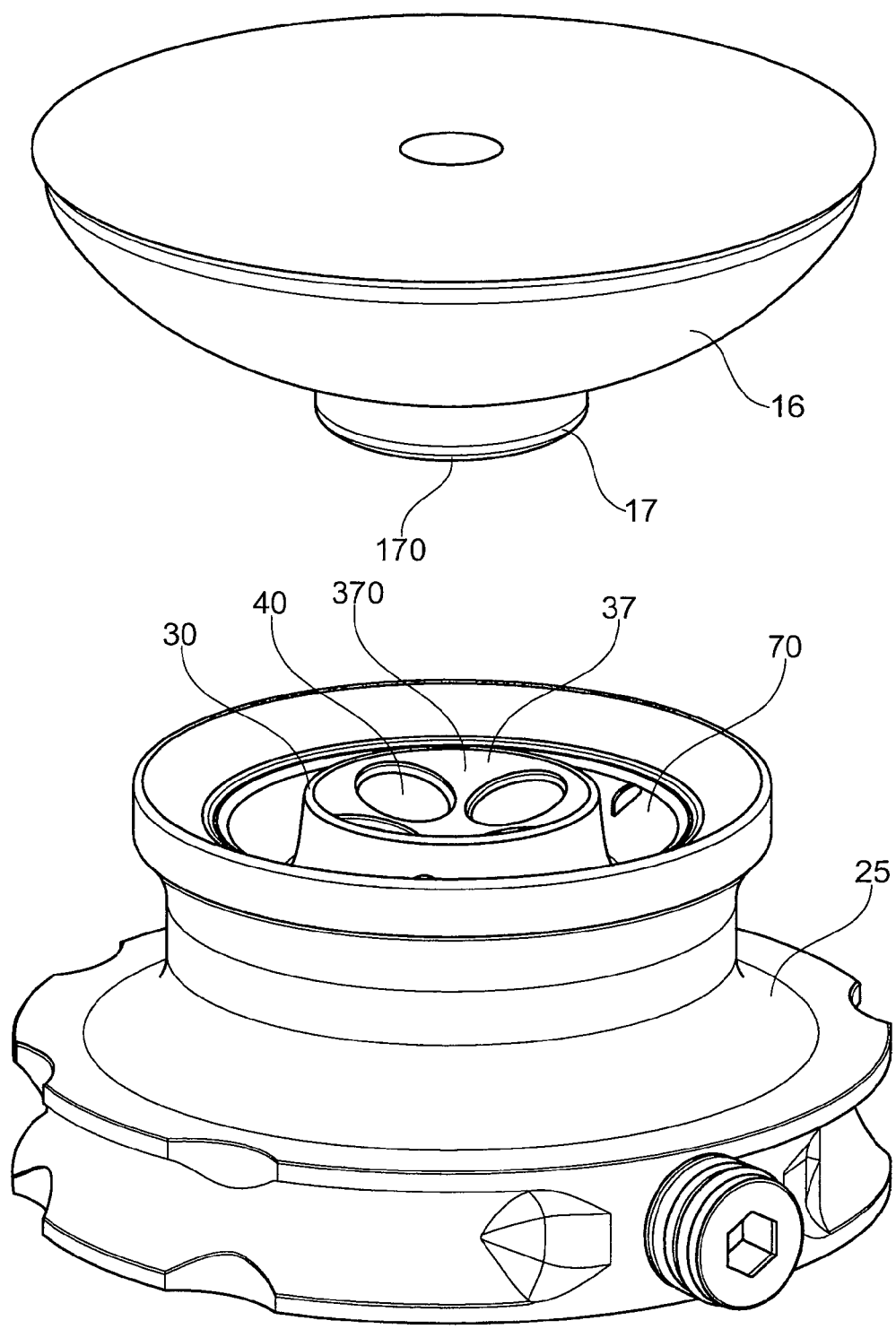
FIG. 9 shows an individual view of the receiving part with pneumatic piston and end cap.

FIG. 9 shows a perspective view of parts of the prosthetic socket system with an end cap 16, which is shown without the associated prosthetic liner. The attachment mechanism 17 is arranged on the distal end of the end cap 16 in the form of an attachment stud. The receiving part 25 is shown in isolation, without integration into a prosthetic socket. The pneumatic piston 30 is inserted within the receiving part 25; the proximal end of the pneumatic piston 30 protrudes from the proximal end of the cylinder region of the receiving part 25. An annular pull-out safety 70 is reversibly arranged on the proximal edge of the receiving part 25, which pull-out safety 70 reduces the diameter of the cylinder region within the receiving part and prevents the piston 30 from being pulled out of the receiving part 25 during a pulling-out movement in the proximal direction.

A proximal end region is formed on the piston 30 as an attachment mechanism 37 and has a spherical surface 370 in which four magnets 40 are inserted. The magnets 40 are either also equipped with a spherical surface and are flush with the spherical surface 370 of the attachment element 37 or are inserted so as to be recessed therein.

The attachment mechanism 17 on the end cap 16 has a contact surface 170 formed correspondingly to the spherical surface 370, wherein magnets are either likewise inset in the attachment mechanism 17 or the attachment mechanism 17 is formed as a magnet or at least comprises a magnetic, in particular ferromagnetic material, so that the attachment mechanism 17 can interact with the magnets 40 inside the pneumatic piston 30. Alternatively, it is possible that the pneumatic piston 30 has a convexly curved, spherical surface 370 at the proximal end, and the contact surface 170 has a concave formation corresponding thereto. It is also possible that the magnets or only one magnet are/is arranged on the attachment element 17 of the prosthetic liner or the distal end cap 16, and the pneumatic piston 30 is ferromagnetic.

Figure 10:
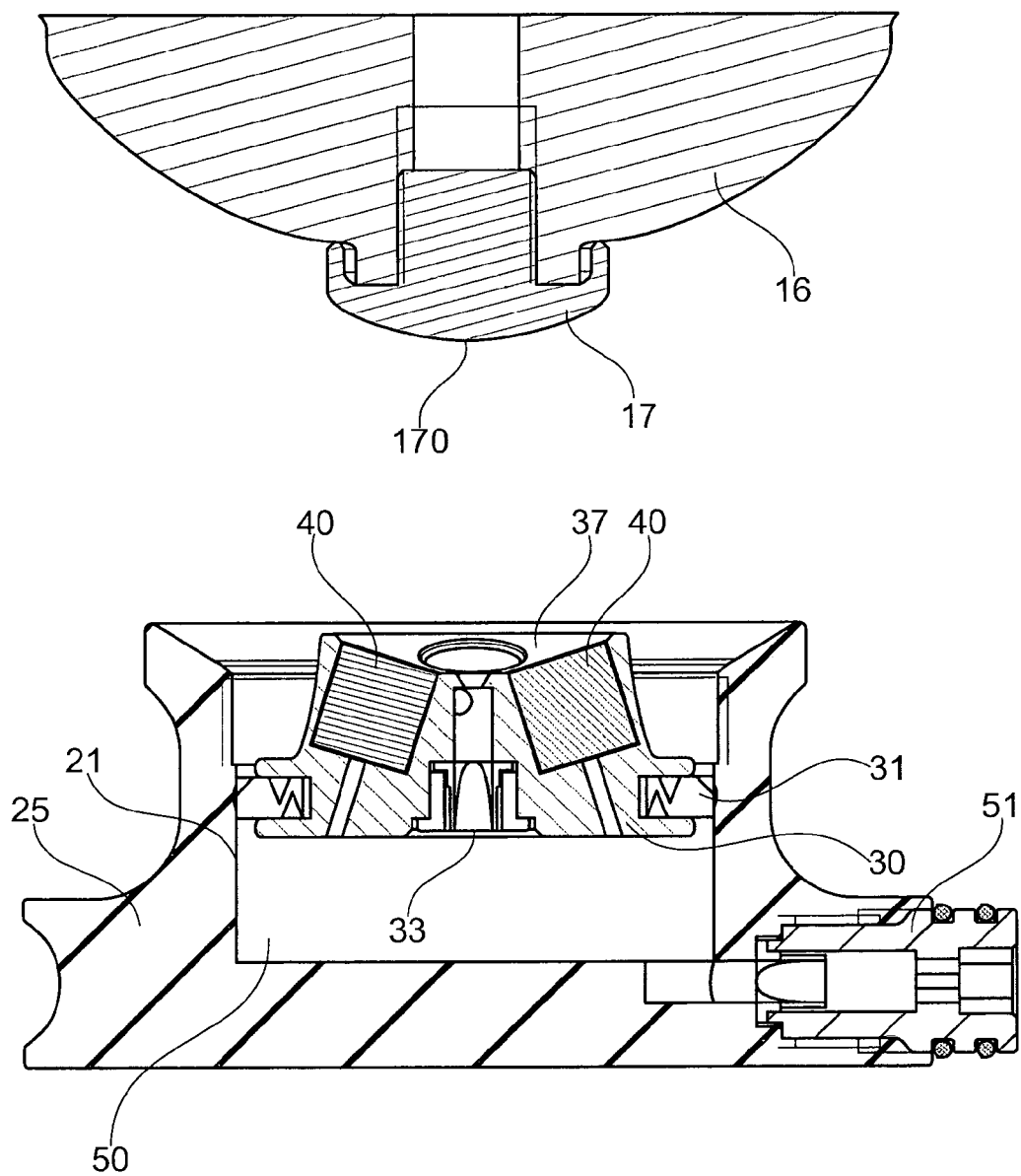
FIG. 10 shows a schematic sectional view in a first variant.

FIG. 10 shows the end cap 16 with the attachment element 17 screwed therein and the spherically formed contact surface in a sectional view; the cylindrical region 21 can likewise be seen in the receiving part 25, as can the pneumatic piston 30 arranged thereon with the radially acting seal 31 and the magnets 40 mounted in the pneumatic piston 30 in the attachment mechanism 37. The magnets 40 are advantageously poled in the same direction, so that they ensure a secure association with the attachment stud 17 and the contact surface 170, independently of the rotational direction or rotational orientation of the pneumatic piston 30 within the receiving part 25. Alternatively, it is possible to equip the magnets 40 with an alternating polarity and to provide a correspondingly differently poled magnet arrangement on the attachment element 17, so that a substantially equal alignment of pneumatic piston 30 and prosthetic liner 10 is ensured after engaging contact.

The closed volume 50 is formed below the piston 30, a valve 33 is provided within the piston 30, a channel with an outlet valve 51 branches off from the closed volume 50, so that the air can escape from the closed volume. The air can be suctioned out of the prosthetic socket or the prosthetic liner by means of the pneumatic piston 30.

Figure 11:
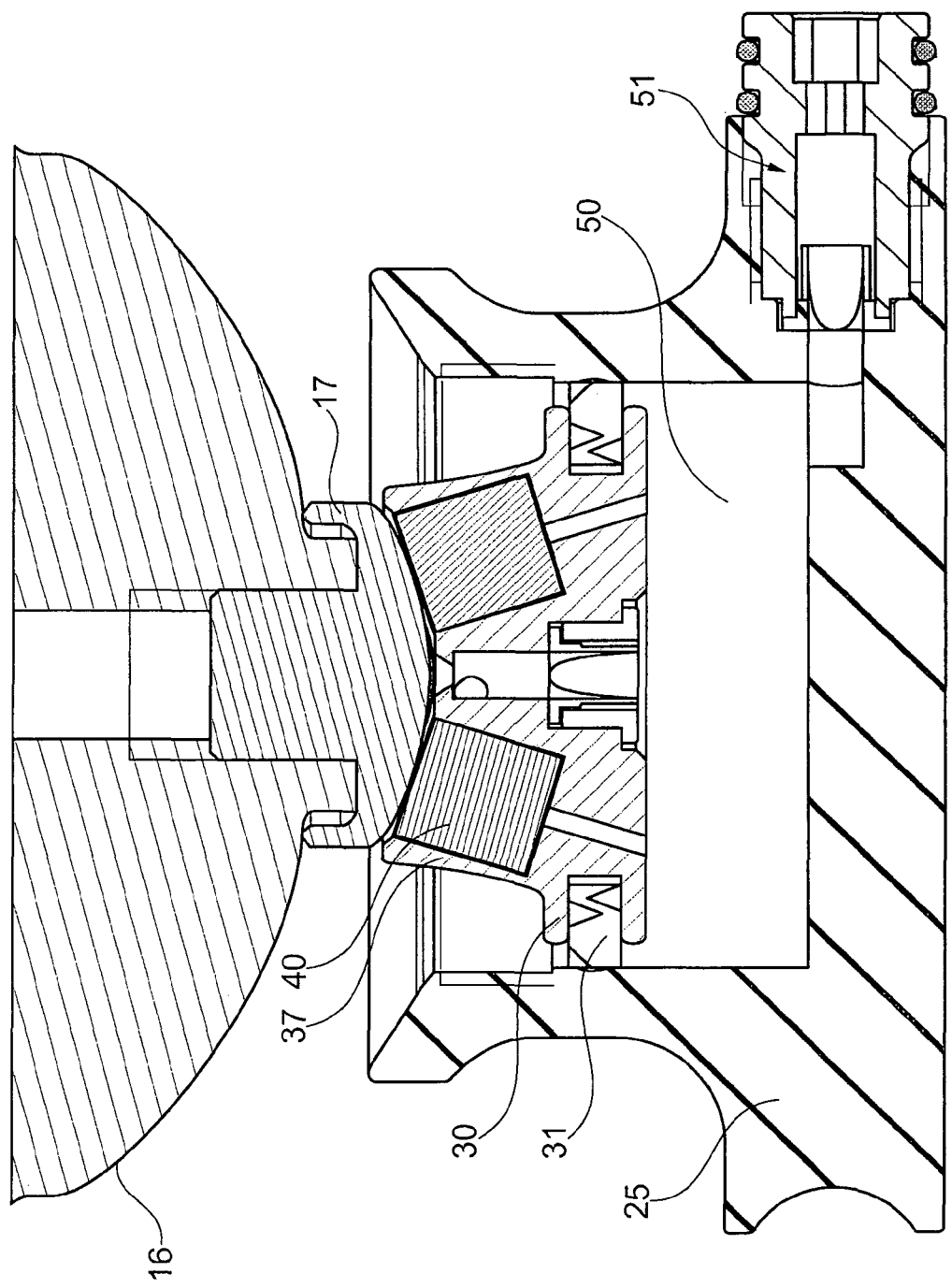
FIG. 11 shows a schematic sectional view of the prosthetic liner in the assembled state.

FIG. 11 shows the embodiment of FIG. 10 in the assembled state. The pneumatic piston 30 is located in the upper position, the magnets 40 pull the attachment element 17 toward the piston 30 and the contact surface 170 is in complete contact with the spherical surface 370 of the piston-side attachment mechanism 37.

Figure 12:
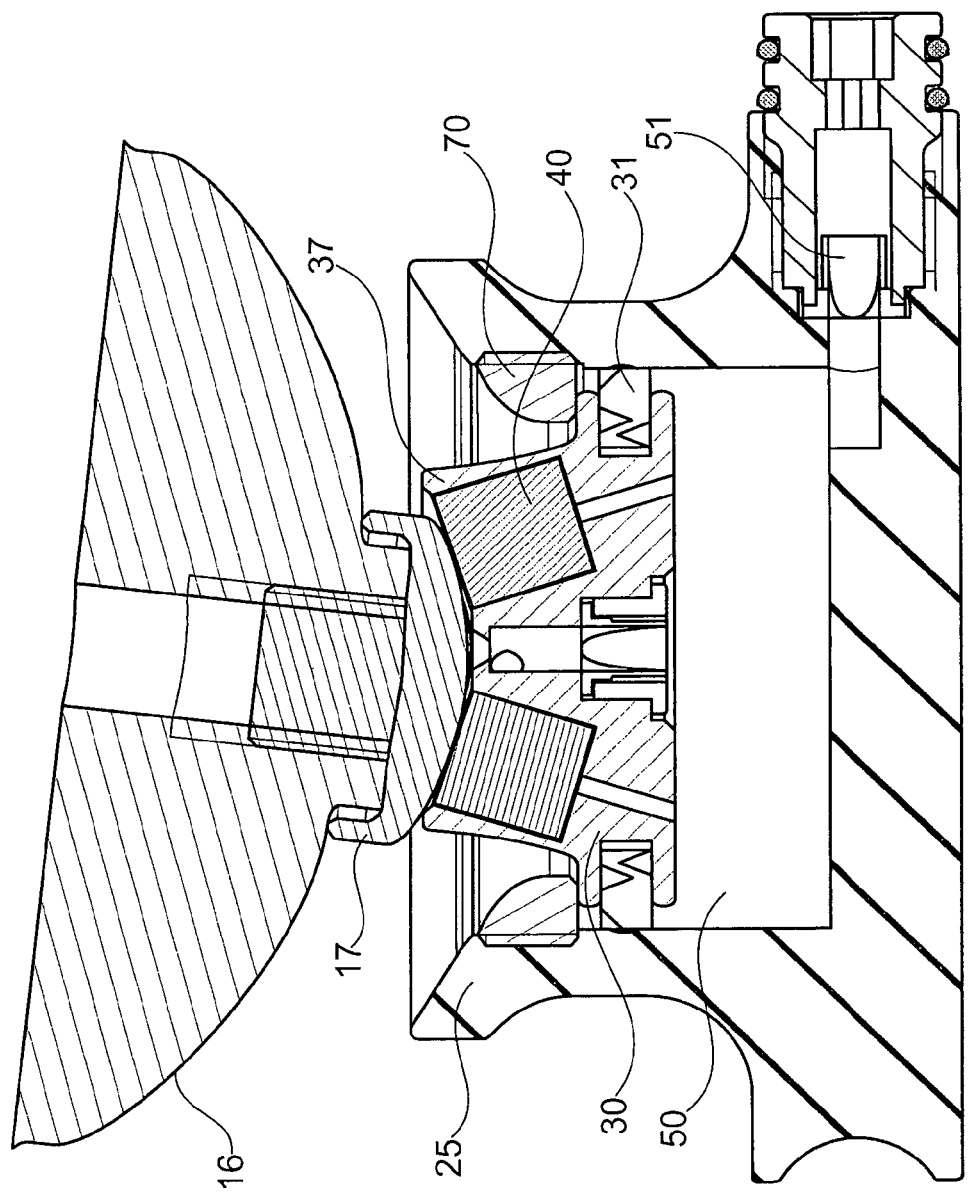
FIG. 12 shows a representation of a tilted position with pull-out safety.

FIG. 12 shows the arrangement according to FIG. 11 with the mounted pull-out safety 70, which is arranged in the receiving part 25, for example screwed in. The upper edge of the pneumatic piston 30 rests against the lower edge of the pull-out safety, as is the case for example during a swing phase. The end cap 16 is slightly tilted to the vertical axis, so that the contact surface 170 is displaced on the spherical surface 370 without losing contact. Due to the curved surfaces, it is possible that a relative movement, in particular a tilting about three pivot axes which intersect at the center of the spherical surface 370, is possible without any problem.

Figure 13:
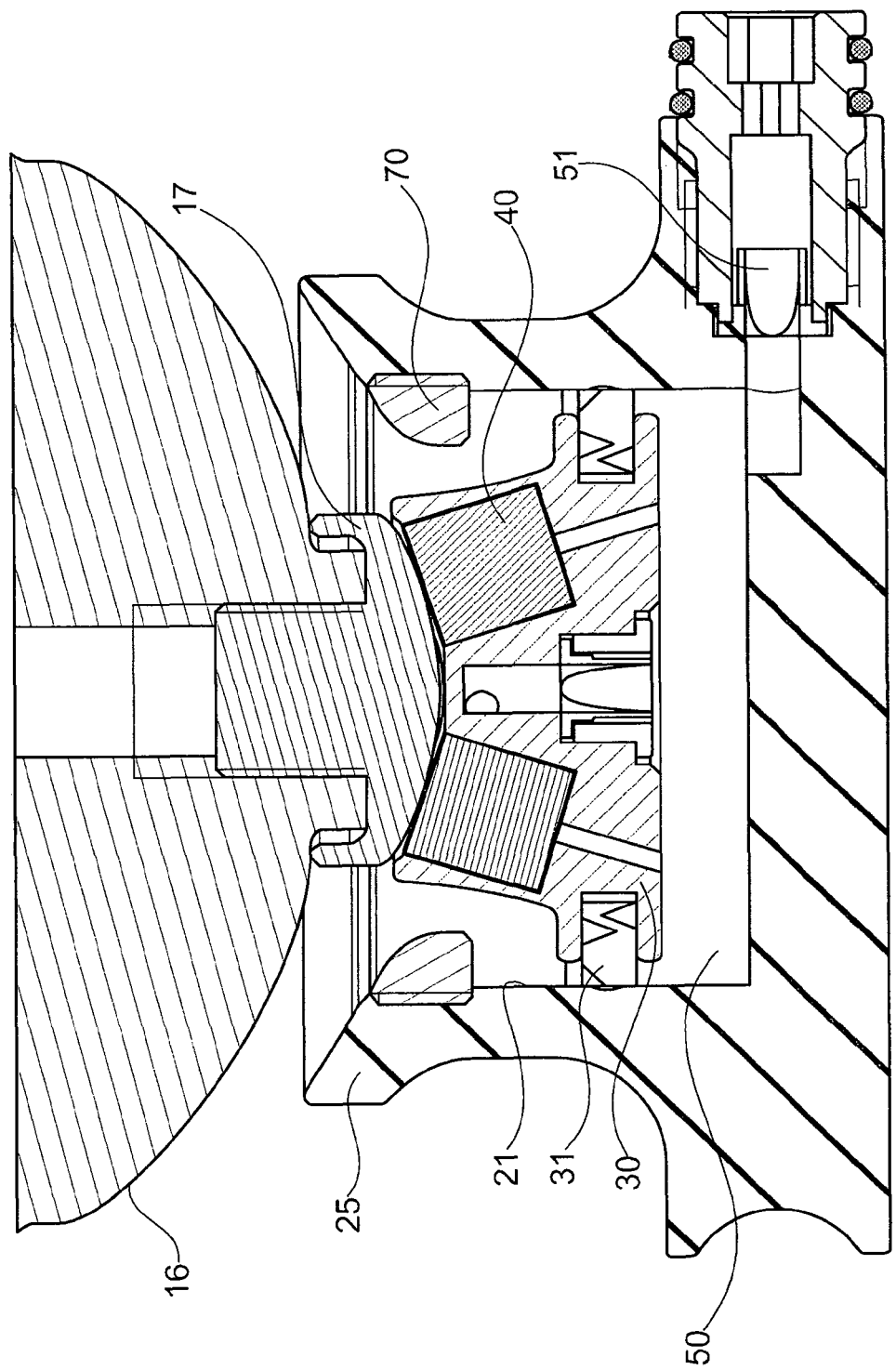
FIG. 13 shows a representation of FIG. 12 in a lowered position.

FIG. 13 shows the arrangement according to FIG. 11 together with the pull-out safety 70 in the central, lowered position; the piston is displaced downward in the direction of the distal end of the cylinder region 21; the closed volume 50 is reduced and the air has been pressed out of the outlet valve 51.

Figure 14:
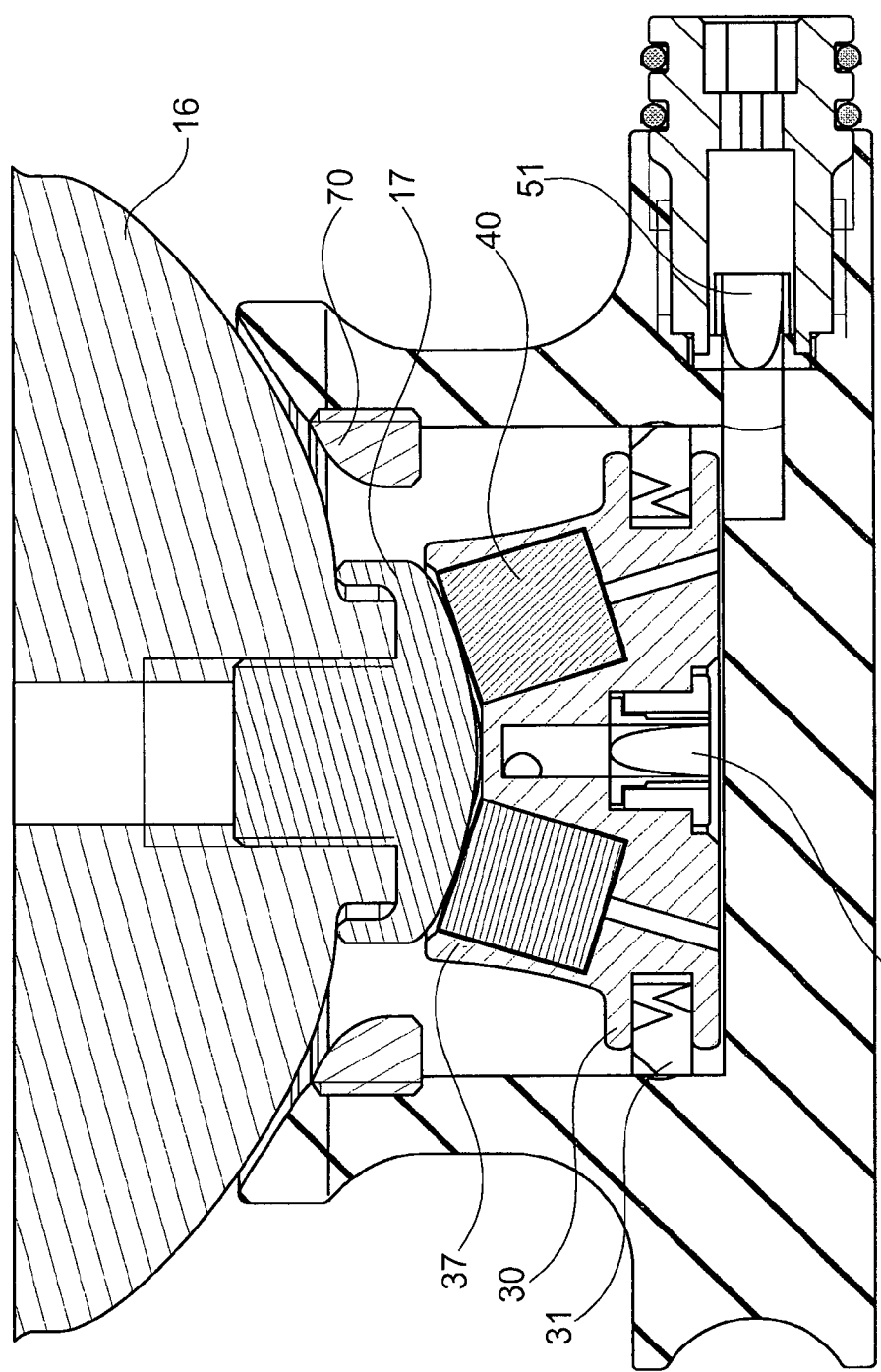
FIG. 14 shows a representation of FIG. 13 in the lowest end position.

FIG. 14 shows the embodiment according to FIG. 13 in the distal end position; the piston 30 is almost in contact with the cylinder base, the closed volume 50 is minimal. The end cap 16 is almost in contact with the proximal end of the receiving part 25.

The maximum piston stroke of the pneumatic piston 30 can be set via the screw-in height or screw-in depth of the attachment element 17 in the end cap 16. If, during an unloading, for example during the swing phase, the pneumatic piston 30 is again displaced in the direction of the pull-out safety 70, air flows either from the prosthetic socket 20 or the prosthetic liner 10 through the valve 30 into the increasing, closed volume 50. In an opposite movement, for example during the stance phase, the closed volume 50 is again reduced, and the suctioned air is pressed out.

Figure 15:
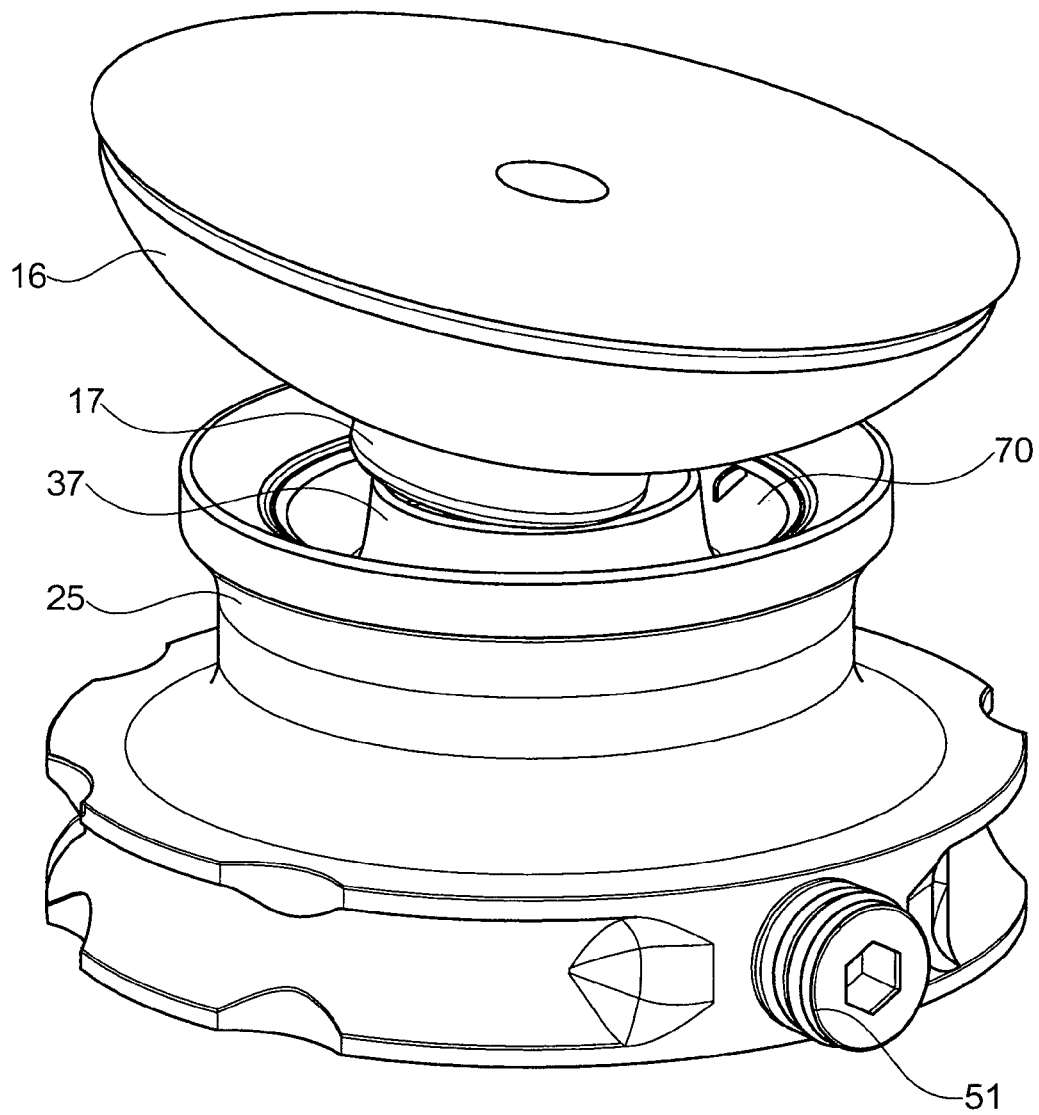
FIG. 15 shows a perspective representation of the position according to FIG. 12.

FIG. 15 shows the arrangement according to FIG. 12 in an oblique view; the end cap 16 is tilted to the vertical axis, the pull-out safety 70 lies annularly about the cylinder region 21 of the receiving part 25 and prevents a situation in which, with separation of the force-locking connection between the prosthetic liner 10 and the pneumatic piston 30, the pneumatic piston 30 is moved out of the receiving part 25.

Figure 16:
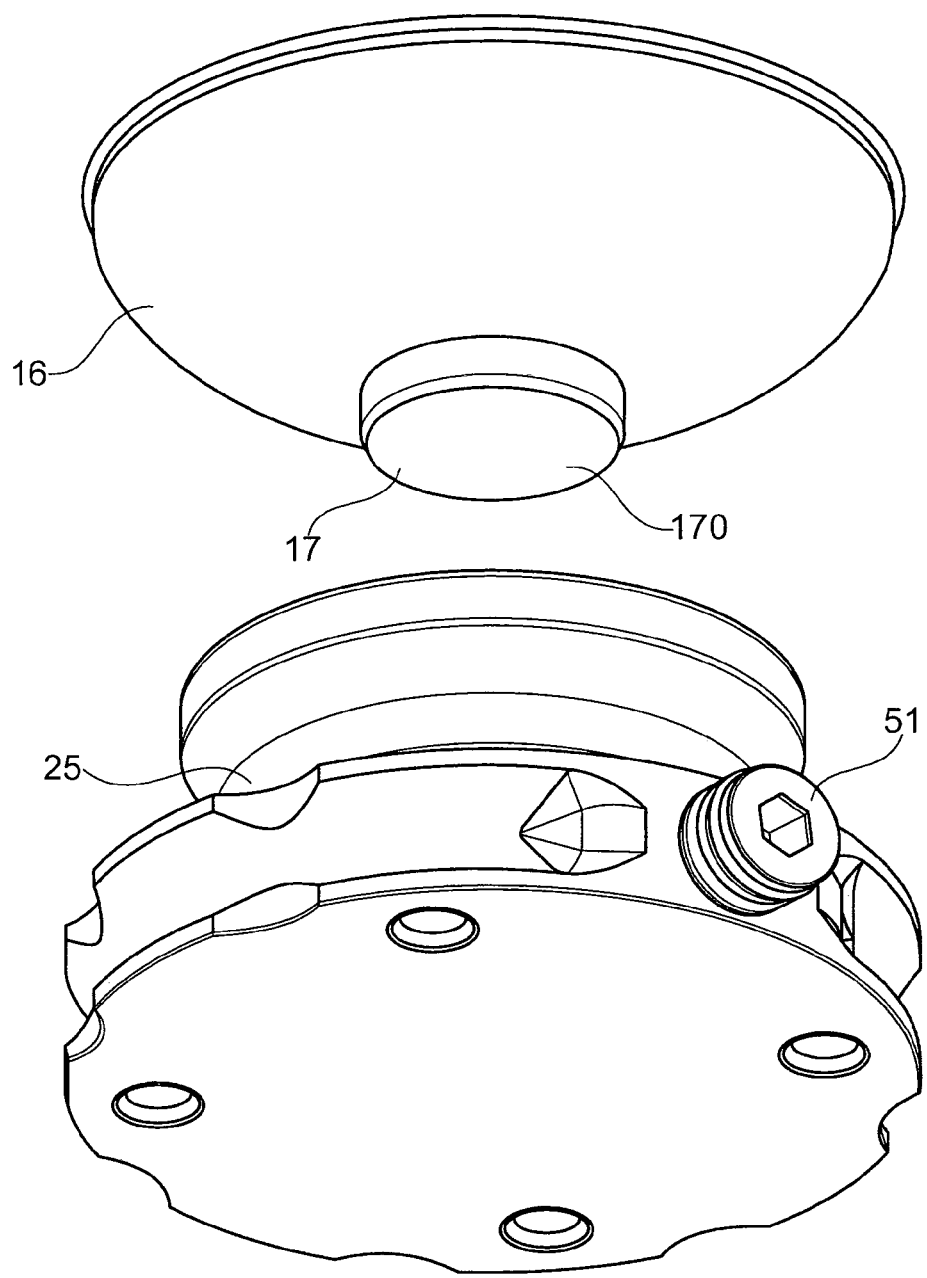
FIG. 16 shows an oblique bottom view of the position according to FIG. 10.

FIG. 16 shows a bottom view of the end cap 16 with the convex, spherical contact surface 170 and the underside of the receiving part 25 with the outlet valve 51.

Figure 17:
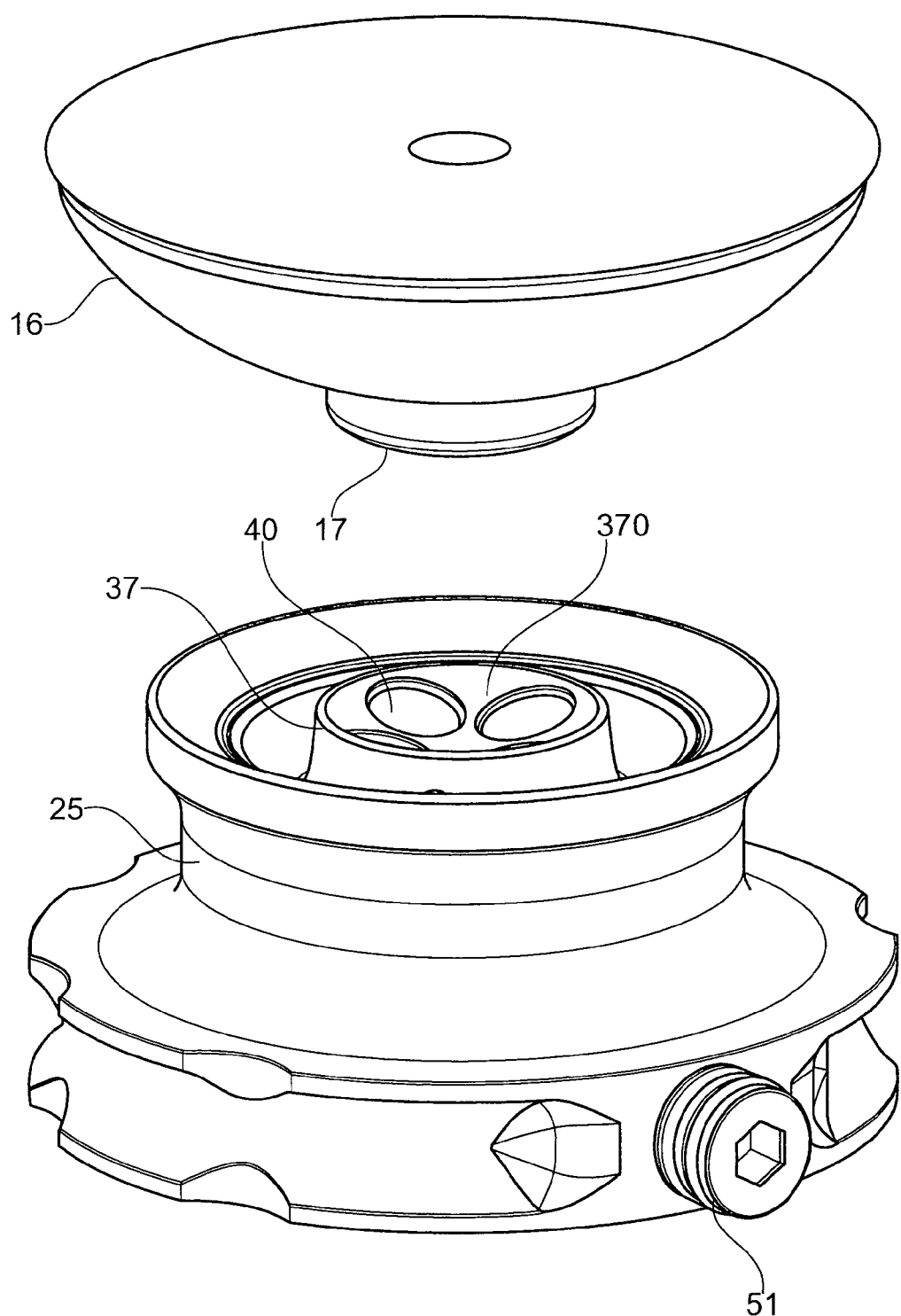
FIG. 17 shows an oblique view of the position according to FIG. 16.

FIG. 17 shows the arrangement according to FIG. 16 in an oblique perspective top view. The at least partially spherical surface 370 of the proximal end of the pneumatic piston 30 in the region of the attachment mechanism 37 can be seen, as can the recessed magnets 40.

Figure 18:
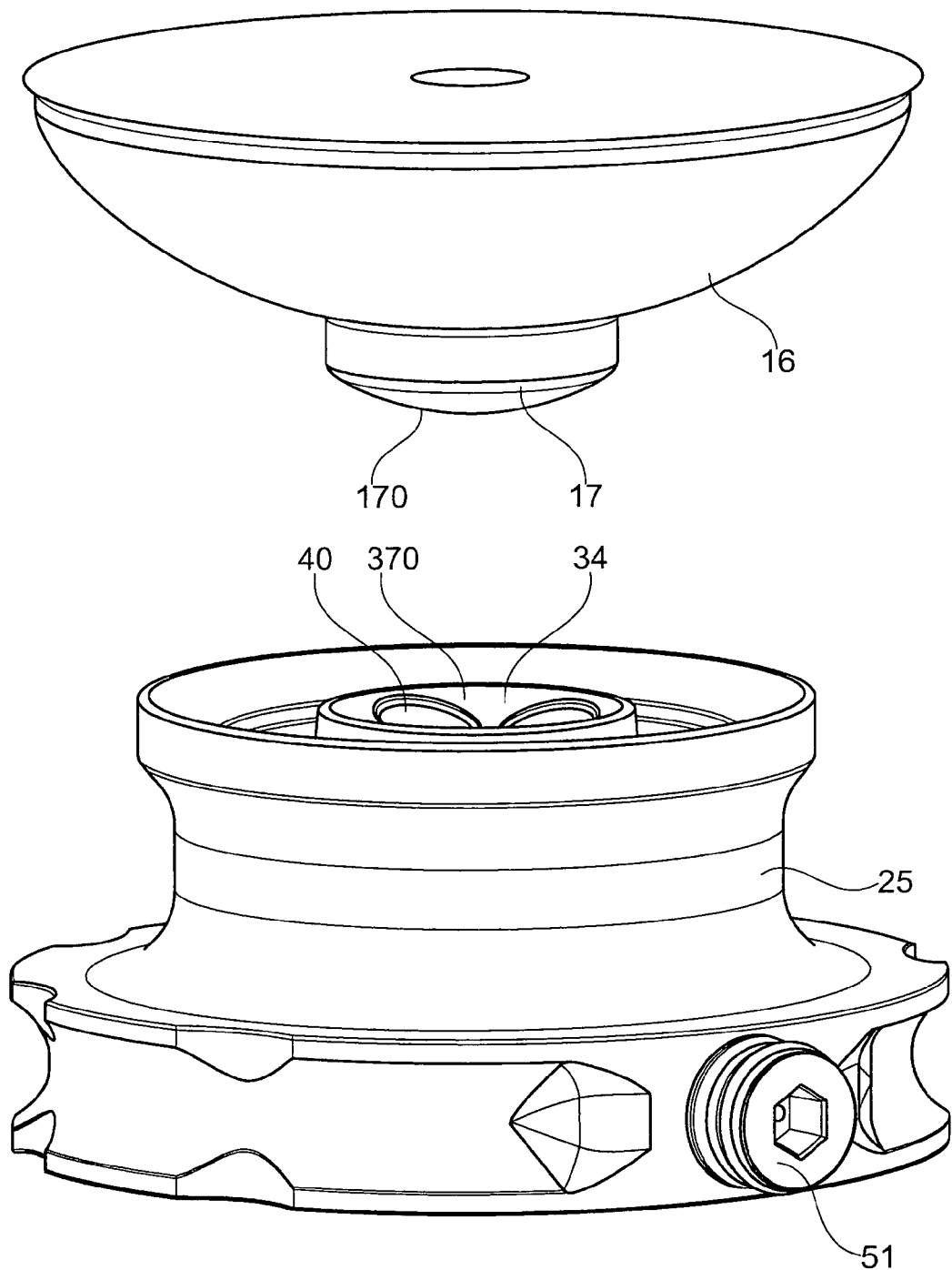
FIG. 18 shows a side view of the position according to FIG. 17.

FIG. 18 shows the arrangement according to FIG. 17 in an oblique side view.

Figure 19:
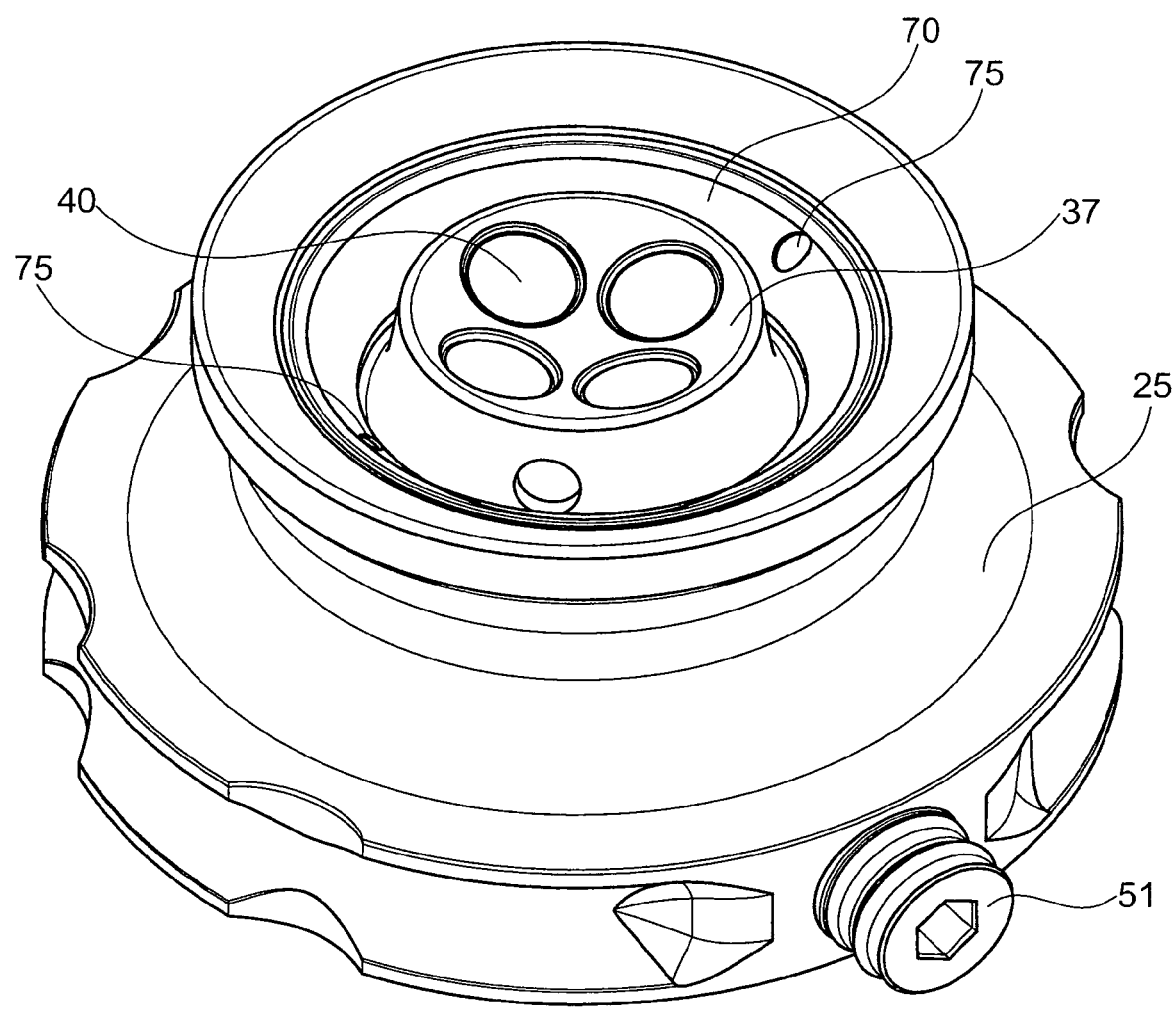
FIG. 19 shows an oblique top view of a receiving part with inserted pneumatic piston and pull-out safety.

FIG. 19 shows the receiving part 25 in a perspective individual representation. It can be seen that the pull-out safety 70 has two opposite recesses 75, into which a tool can engage in order to attach the pull-out safety 70 to the receiving part 25 in the region of the cylinder wall. In addition to a screwing into a thread which is formed in the cylinder section, wherein the pull-out safety 70 has an outer thread, the pull-out safety 70 may also be screwed or attached and positively held via separate screws or attachment means to the receiving part 25.

Figure 20:
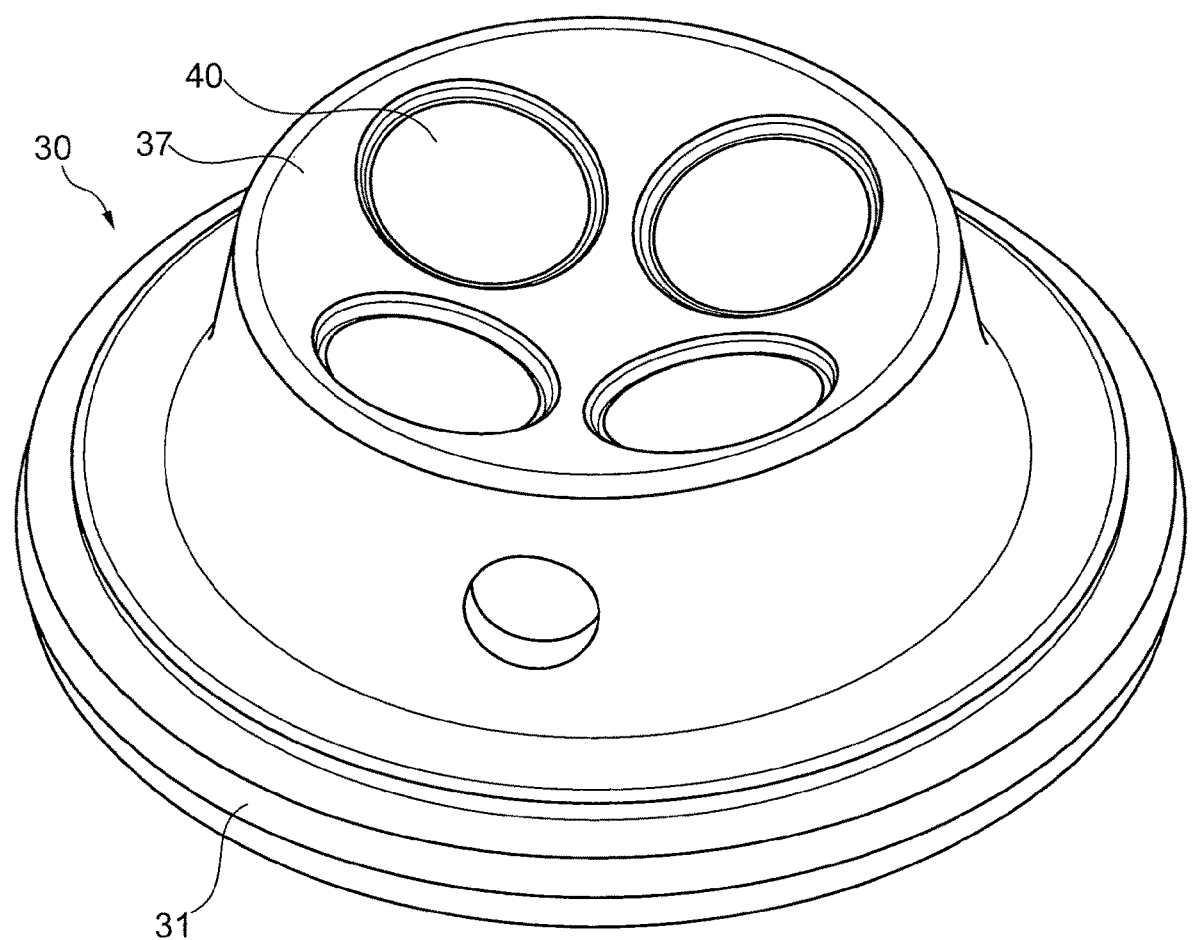
FIG. 20 shows an individual representation of a pneumatic piston.

FIG. 20 shows the pneumatic piston 30 in an individual representation with the four magnets arranged therein, the attachment mechanism 37 with the spherical surface 370 and the radially arranged sealing element 31 in the form of a sealing ring.

Figure 21:
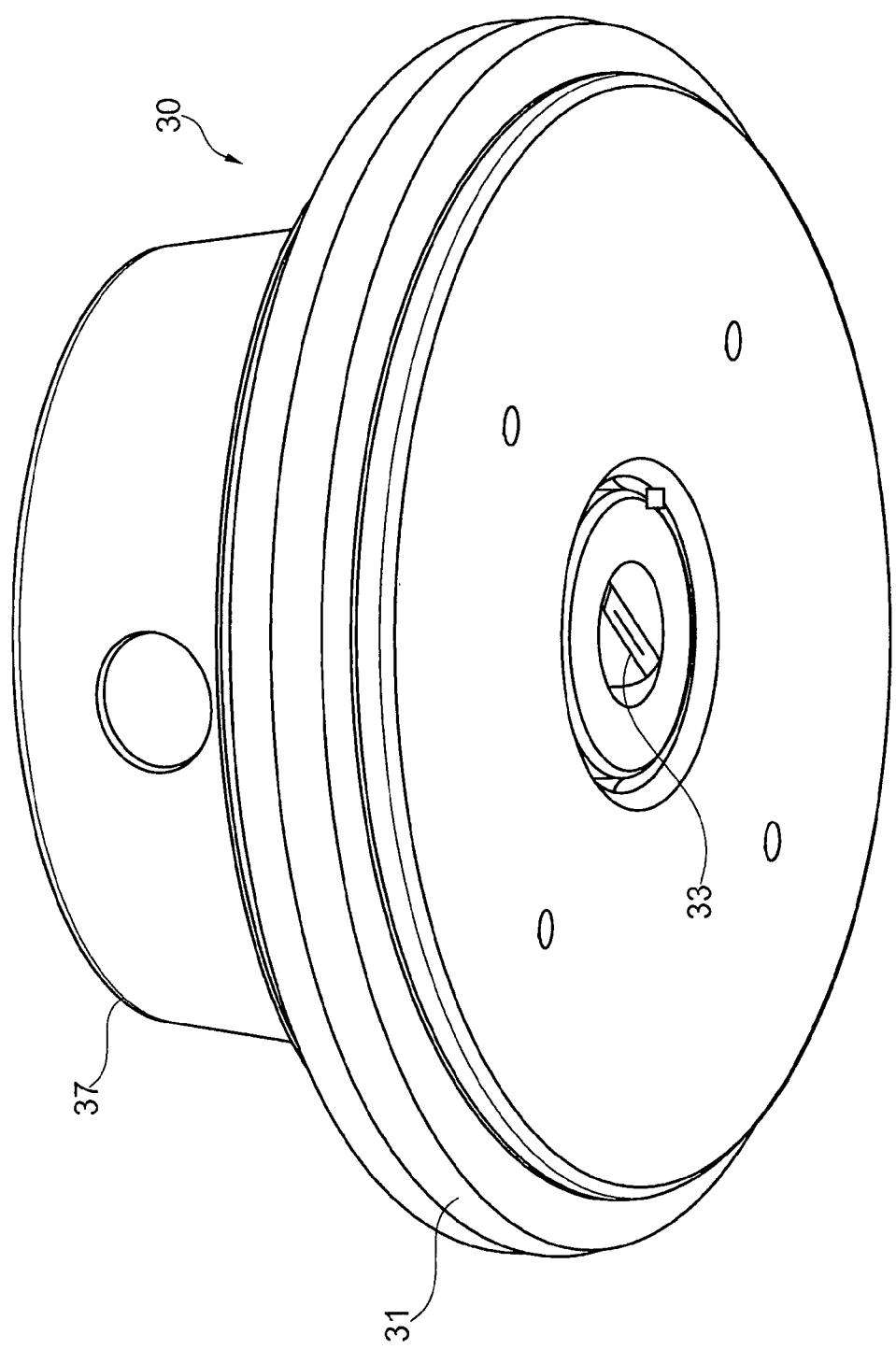
FIG. 21 shows an oblique bottom view of the pneumatic piston according to FIG. 20.

FIG. 21 shows the pneumatic piston 30 in a bottom view with the valve 33, which allows an inflow of air into the closed volume 50 but prevents a reverse flow. The valve 33 may be formed as a hose valve or reed valve and serves as a non-return valve.

Figure 22:
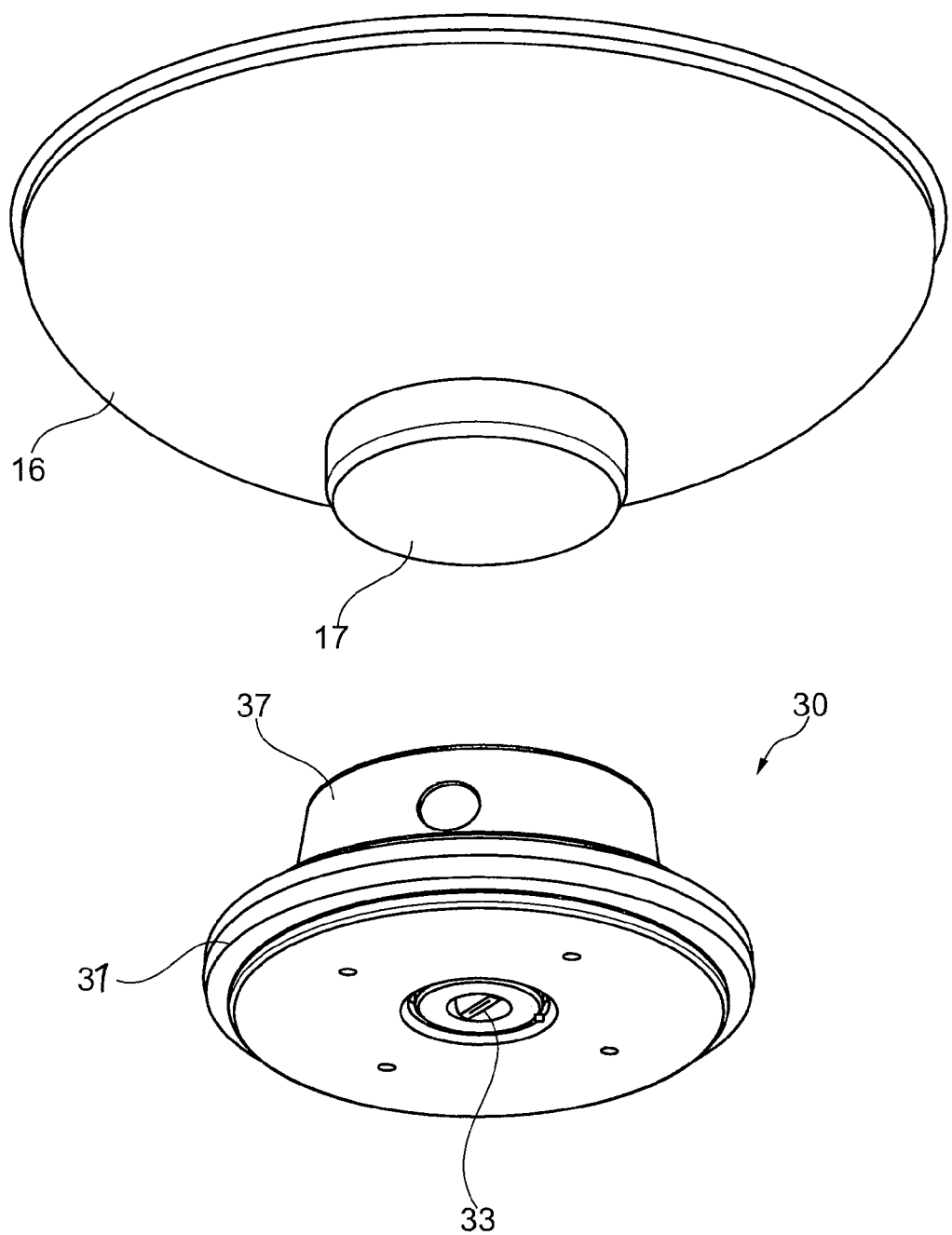
FIG. 22 shows an oblique bottom view of an end cap and a pneumatic piston.

FIG. 22 shows the arrangement of the end cap 16 with the attachment element 17 as an attachment piston and the pneumatic piston 30 obliquely from below.

Figure 23:
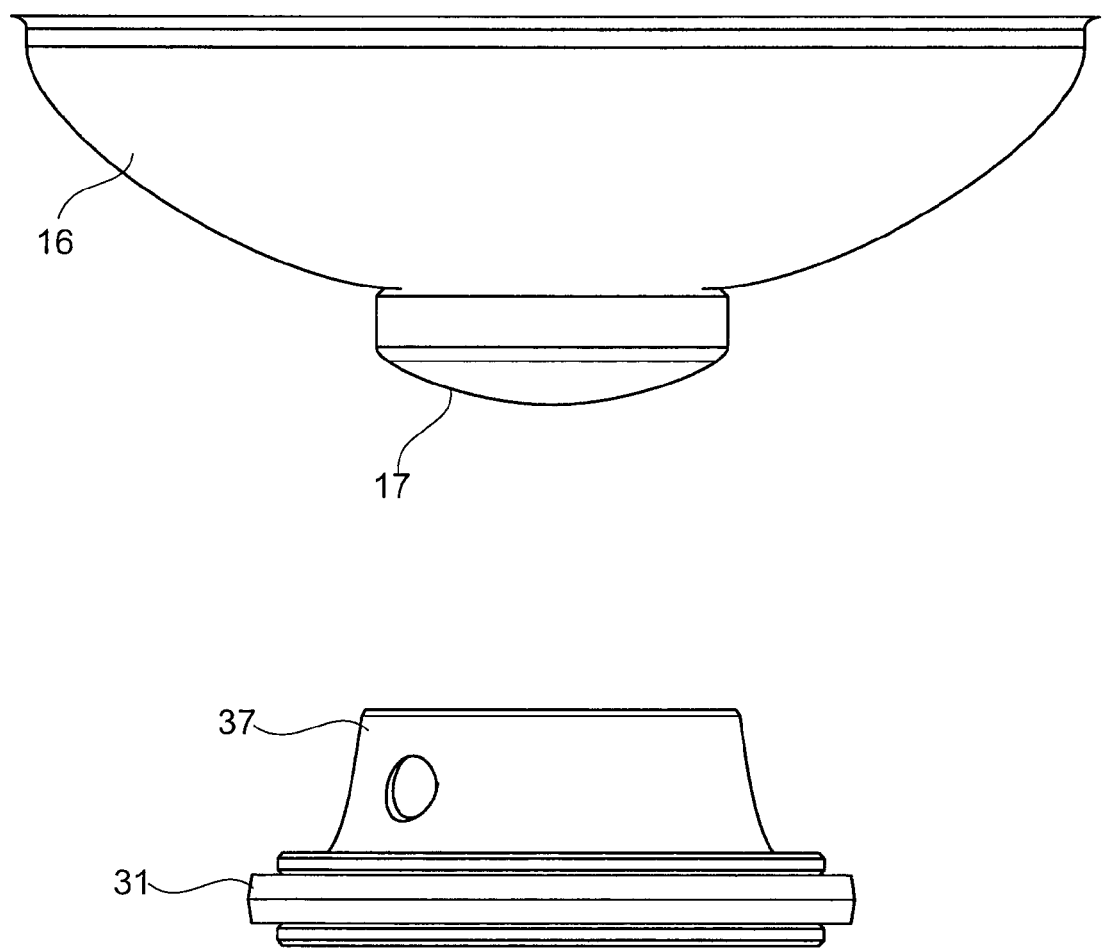
FIG. 23 shows a side view of the position according to FIG. 22.

FIG. 23 shows the pneumatic piston 30 with the attachment element 37, the sealing ring 31 before joining to the distal end cap 16.

The invention claimed is:

1. A prosthetic liner for application on a stump, comprising:
   an elastic base body which has a proximal opening for insertion of the stump into a receiving space, and a closed distal end;
   at least one pneumatic piston being attached to an exterior surface of the base body at the closed distal end, the at least one pneumatic piston and the elastic base body together because of the attachment being insertable into and removable from a prosthetic socket and movable within the prosthetic socket to generate a vacuum condition during reciprocal movement of the elastic base body and piston within the socket, the elastic base body and piston remaining attached during the reciprocal movement, the at least one piston comprising a one way valve to prevent a reverse flow of air to the base body.

2. The prosthetic liner as claimed in claim 1, wherein the at least one pneumatic piston is reversibly attached at the distal end.

3. The prosthetic liner as claimed in claim 1, further comprising a dimensionally stable end cap positioned on the exterior surface of the base body at the distal end.

4. The prosthetic liner as claimed in claim 3, wherein the at least one pneumatic piston is formed as a separate component and is attached to the end cap.

5. The prosthetic liner as claimed in claim 1, wherein the at least one pneumatic piston has at least one circumferential sealing element.

6. The prosthetic liner as claimed in claim 1, wherein the at least one pneumatic piston is movably attached to the prosthetic liner.

7. The prosthetic liner as claimed in claim 1, wherein the at least one pneumatic piston is attached to the prosthetic liner via a ball joint or an elastic connection.

8. The prosthetic liner as claimed in claim 1, wherein the at least one pneumatic piston is attached to the prosthetic liner via at least one magnet.

9. The prosthetic liner as claimed in claim 8, wherein the at least one pneumatic piston is connectably integrated via at least one magnet into a prosthetic socket system composed of the prosthetic liner and a prosthetic socket.

10. The prosthetic liner as claimed in claim 8, wherein the at least one pneumatic piston has an at least partially spherical surface.

11. The prosthetic liner as claimed in claim 8, further comprising an attachment element arranged on the prosthetic liner, via which the at least one pneumatic piston is attached to the prosthetic liner and which has a contact surface formed to correspond to an at least partially spherical surface of the at least one pneumatic piston.

12. The prosthetic liner as claimed in claim 1, wherein the at least one pneumatic piston is positively attached directly to the exterior surface of the base body at the closed distal end, or is positively attached to the exterior surface of the base body with an intervening member.

13. A prosthetic socket system comprising:
   a prosthetic liner configured to mount to a residual limb, the prosthetic liner comprising an elastic base body which has a proximal opening for insertion of the residual limb into a receiving space, and a closed distal end;
   a prosthetic socket, comprising:
      an internal cavity configured to receive the residual limb to which the prosthetic liner has been mounted, an intermediary space being provided within the internal cavity between the prosthetic socket and the prosthetic liner;
      a receiving member having a cylinder region and an outlet valve in flow communication with the cylinder region, the cylinder region having an open proximal end and closed distal end;
   at least one pneumatic piston being attached to an exterior surface of the prosthetic liner at the closed distal end, the at least one pneumatic piston and the prosthetic liner together being insertable with the residual limb into the prosthetic socket to position the prosthetic liner in the internal cavity and the at least one pneumatic piston within the cylinder region, the prosthetic liner and the at least one pneumatic piston being movable together as an attached assembly to generate a vacuum condition;
   a return valve in flow communication with the intermediary space;
   the cylinder region receives the at least one pneumatic piston and the at least one pneumatic piston slides along an inner surface of the cylinder region when the prosthetic liner is connected to the prosthetic socket, a closed volume being formed between the at least one pneumatic piston and the distal end of the cylinder region, the closed volume being in flow communication with the return valve, the return valve being operable to permit a flow of air from the intermediary space into the closed volume and prevent a reverse flow of air into the intermediary space.

14. The prosthetic socket system as claimed in claim 13, wherein the closed volume has a fluidic connection to the outlet valve, which enables an outflow of air from the closed volume and prevents a reverse flow into the closed volume.

15. The prosthetic socket system as claimed in claim 13, wherein at least one of the closed volume and the intermediary space are fluidically connected to ambient air.

16. The prosthetic socket system as claimed in claim 13, wherein the return valve is arranged in the at least one pneumatic piston.

17. The prosthetic socket system as claimed in claim 13, wherein the cylinder region has an insertion bevel at its proximal end.

18. The prosthetic socket system as claimed in claim 13, wherein a pull-out safety for the at least one pneumatic piston is arranged at the proximal end of the cylinder region.

19. The prosthetic liner as claimed in claim 13, wherein the return valve is positioned in the receiving member.

20. The pneumatic socket system as claimed in claim 13, wherein the prosthetic liner and the at least one pneumatic piston are movable together as an attached assembly to generate a vacuum condition during reciprocal movement of the elastic base body and at least one pneumatic piston within the socket, the elastic base body and at least one pneumatic piston remaining attached during the reciprocal movement.

21. A prosthetic liner for application on a residual limb, comprising:
   an elastic base body, comprising:
      a receiving space configured to receive the residual limb;
      a proximal opening for insertion of the residual limb into the receiving space;
      a closed distal end;
      an attachment element attached to an exterior surface of the elastic base body;
   a pneumatic piston releasably mounted to the attachment element with an attachment, the pneumatic piston, the attachment element and the elastic base body together as an assembly being insertable with the residual limb into a prosthetic socket to position the elastic base body and the attachment element in an internal cavity of the prosthetic socket and position the pneumatic piston within a cylinder carried by the prosthetic socket, the assembly being movable relative to the prosthetic socket and cylinder to generate a vacuum condition during reciprocal movement of the elastic base body and pneumatic piston within the socket, the elastic base body and pneumatic piston remaining attached during the reciprocal movement.

22. The prosthetic liner as claimed in claim 21, wherein the pneumatic piston includes a one way valve to prevent a reverse flow of air to the base body.

23. The prosthetic liner as claimed in claim 22, further comprising at least one magnet operable to releasably connect the pneumatic piston to the attachment element.

* * * * *